United States Patent
Demmer et al.

(10) Patent No.: US 11,420,067 B2
(45) Date of Patent: Aug. 23, 2022

(54) MEDICAL DEVICE AND METHOD FOR CONTROLLING PACING INTERVAL TO PROMOTE MECHANICAL HEART CHAMBER SYNCHRONY

(71) Applicant: Medtronic, Inc., Minneapolis, MN (US)

(72) Inventors: Wade M. Demmer, Coon Rapids, MN (US); Alexander R. Mattson, St. Paul, MN (US); Todd J. Sheldon, North Oaks, MN (US); Zhongping Yang, Woodbury, MN (US)

(73) Assignee: Medtronic, Inc., Minneapolis, MN (US)

(*) Notice: Subject to any disclaimer, the term of this patent is extended or adjusted under 35 U.S.C. 154(b) by 177 days.

(21) Appl. No.: 16/833,965

(22) Filed: Mar. 30, 2020

(65) Prior Publication Data

US 2020/0316386 A1    Oct. 8, 2020

Related U.S. Application Data

(60) Provisional application No. 62/830,020, filed on Apr. 5, 2019.

(51) Int. Cl.
| | | |
|---|---|---|
| *A61N 1/365* | (2006.01) | |
| *A61N 1/368* | (2006.01) | |
| *A61N 1/37* | (2006.01) | |
| *A61N 1/39* | (2006.01) | |

(52) U.S. Cl.
CPC ....... *A61N 1/36592* (2013.01); *A61N 1/3684* (2013.01); *A61N 1/36578* (2013.01); *A61N 1/3706* (2013.01); *A61N 1/39622* (2017.08)

(58) Field of Classification Search
None
See application file for complete search history.

(56) References Cited

U.S. PATENT DOCUMENTS

| | | |
|---|---|---|
| 5,584,868 A | 12/1996 | Salo et al. |
| 5,609,612 A | 3/1997 | Plicchi et al. |
| 7,079,896 B1 | 7/2006 | Park et al. |
| 7,092,759 B2 | 8/2006 | Nehls et al. |
| 7,664,547 B2 | 2/2010 | Plicchi et al. |
| 7,689,283 B1 | 3/2010 | Schecter |
| 8,150,513 B2 | 4/2012 | Chinchoy et al. |
| 8,214,041 B2 | 7/2012 | Van Gelder et al. |
| 9,119,959 B2 | 9/2015 | Rys et al. |
| 9,675,798 B2 | 6/2017 | Grubac et al. |
| 9,999,775 B2 | 6/2018 | Ghosh |
| 2011/0093027 A1 | 4/2011 | Renesto et al. |
| 2013/0325081 A1 | 12/2013 | Karst et al. |

(Continued)

OTHER PUBLICATIONS

A0001137US02 (PCT/US2020/025965) PCT Notification of Transmittal of the International Search Report and the Written Opinion of the International Searching Authority, dated Jun. 30, 2020, 9 pages.

*Primary Examiner* — Brian T Gedeon

(57) ABSTRACT

A medical device includes a motion sensor for producing a motion signal including cardiac event signals. The medical device generates a ventricular pacing pulse upon expiration of a pacing interval. The medical device determines a synchrony metric from the motion signal after a delivered ventricular pacing pulse and adjusts the pacing interval based on the synchrony metric.

29 Claims, 10 Drawing Sheets

(56) References Cited

U.S. PATENT DOCUMENTS

| | | | |
|---|---|---|---|
| 2017/0274213 A1 | 9/2017 | Ghosh et al. | |
| 2018/0085588 A1* | 3/2018 | Splett | A61N 1/3682 |
| 2018/0117337 A1* | 5/2018 | Demmer | A61N 1/3684 |
| 2018/0161580 A1* | 6/2018 | Demmer | A61N 1/36514 |
| 2019/0009095 A1* | 1/2019 | Sheldon | A61N 1/3756 |
| 2019/0083779 A1 | 3/2019 | Yang et al. | |
| 2019/0083800 A1 | 3/2019 | Yang et al. | |
| 2019/0134404 A1 | 5/2019 | Sheldon et al. | |
| 2019/0134405 A1 | 5/2019 | Sheldon et al. | |
| 2019/0308022 A1* | 10/2019 | Demmer | A61N 1/36578 |
| 2020/0146580 A1* | 5/2020 | Sarkar | A61N 1/3621 |

\* cited by examiner

MEDICAL DEVICE AND METHOD FOR CONTROLLING PACING INTERVAL TO PROMOTE MECHANICAL HEART CHAMBER SYNCHRONY

REFERENCE TO RELATED APPLICATIONS

This application claims the benefit of U.S. Patent Application No. 62/830,020, filed provisionally on Apr. 5, 2019 and incorporated herein by reference in its entirety.

TECHNICAL FIELD

The disclosure relates generally to implantable medical devices and in particular to an intracardiac pacemaker and method for controlling pacing intervals based on an intracardiac motion signal to promote mechanical synchrony of the heart chambers.

BACKGROUND

The cardiac conduction system includes the sinus atrial (SA) node, the atrioventricular (AV) node, the bundle of His, bundle branches and Purkinje fibers. A heart beat is initiated in the SA node, which acts as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches and Purkinje fibers.

Patients with a conduction system abnormality, e.g., poor AV node conduction or poor SA node function, may receive a pacemaker to restore a more normal heart rhythm and atrioventricular synchrony. Dual chamber pacemakers are available which include a transvenous atrial lead carrying electrodes which are placed in the right atrium and a transvenous ventricular lead carrying electrodes that are placed in the right ventricle via the right atrium. The pacemaker itself is generally implanted in a subcutaneous pocket with the transvenous leads tunneled to the subcutaneous pocket. A dual chamber pacemaker senses atrial electrical signals and ventricular electrical signals and can provide both atrial pacing and ventricular pacing as needed to promote a normal heart rate and synchronization of the electrical depolarization of the right atrial and right ventricular chambers.

Heart failure patients may experience ventricular dyssynchrony. A multi-chamber pacemaker may deliver cardiac resynchronization therapy (CRT) by pacing the atria and/or one or both ventricles to improve ventricular synchrony in a patient suffering from heart failure or other abnormalities that lead to poor coordination of the ventricular chambers. Transvenous leads may be positioned in the right atrium, right ventricle, and a cardiac vein of the left ventricle to provide sensing and pacing in up to all three heart chambers.

Intracardiac pacemakers have been introduced or proposed for implantation entirely within a patient's heart, eliminating the need for transvenous leads which can be a source of infection or other complications. An intracardiac pacemaker may provide sensing and pacing within a single chamber of the patient's heart. In some patients, single chamber pacing and sensing may adequately address the patient's needs. However single chamber pacing and sensing may not fully address the cardiac conduction disease or abnormalities in all patients. Dual chamber sensing and/or pacing functions may be required to restore a more normal heart rhythm.

SUMMARY

In general, the disclosure is directed to a medical device and method for determining a synchrony metric from a motion signal sensed by a motion sensor. The motion signal includes cardiac event signals. The medical device may be a pacemaker that adjusts a pacing interval to improve mechanical synchrony of the heart chambers based on the synchrony metric. The pacing interval may be an AV pacing interval, also referred to herein as the "AV interval," between atrial events and ventricular pacing pulses to promote optimal mechanical synchrony of the heart chambers. In other examples, the pacing interval may be an interventricular interval, also referred to herein as a "V1-V2 interval" for improving ventricular synchrony. The pacemaker may be a leadless pacemaker, which may be wholly implantable in the right atrium in some examples, capable of sensing atrial events from a cardiac electrical signal or from the motion signal and/or delivering atrial pacing pulses. The pacemaker may be configured to deliver ventricular pacing pulses to ventricular tissue, synchronized to the atrial events at the AV interval. In other examples, the pacemaker may be wholly implantable in a first ventricular chamber and configured to provide pacing pulses to the second, opposing ventricular chamber, synchronized to the first ventricular chamber at an interventricular pacing interval. The pacemaker, operating according to the techniques disclosed herein, senses a motion signal including atrial and ventricular mechanical event signals, determines a synchrony metric from the motion signal, and adjusts the AV pacing interval and/or the interventricular pacing interval based on the synchrony metric to promote optimized heart chamber synchrony. The adjusted pacing interval may be used to deliver atrial synchronized ventricular pacing or CRT by the medical device, as examples.

In one example, the disclosure provides a medical device including a motion sensor configured to produce a motion signal including an atrial systolic event signal, a first ventricular systolic event signal corresponding to an onset of ventricular contraction, and a second ventricular systolic event signal corresponding to an ending of ventricular contraction. The medical device includes a therapy delivery circuit configured to generate ventricular pacing pulses. Each ventricular pacing pulse is generated upon expiration of a pacing interval. The medical device includes a control circuit configured to determine a synchrony metric from the motion signal based on at least one of the first ventricular systolic event signal and/or the second ventricular systolic event signal following at least one generated ventricular pacing pulse. The control circuit may adjust the pacing interval based on the synchrony metric.

In another example, the disclosure provides a method including producing a motion signal including an atrial systolic event signal, a first ventricular systolic event signal corresponding to an onset of ventricular contraction, and a second ventricular systolic event signal corresponding to an ending of ventricular contraction. The method includes generating a ventricular pacing pulse upon expiration of a pacing interval, determining a synchrony metric from the motion signal based on at least one of the first ventricular systolic event signal and/or the second ventricular systolic event signal following at least one ventricular pacing pulse and adjusting the pacing interval based on the synchrony metric.

In another example, the disclosure provides a non-transitory computer-readable storage medium storing a set of instructions, which when executed by a medical device, cause the medical device to produce a motion signal including an atrial systolic event signal, a first ventricular systolic event signal corresponding to an onset of ventricular contraction, and a second ventricular systolic event signal corresponding to an ending of ventricular contraction. The instructions cause the medical device to generate a ventricular pacing pulse upon expiration of a pacing interval. The instructions further cause the medical device to determine a synchrony metric from the motion signal based on at least one of the first ventricular systolic event signal and/or the second ventricular systolic event signal following at least one generated ventricular pacing pulse and adjust the pacing interval based on the synchrony metric.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

A cardiac pacemaker and pacing techniques are disclosed herein for controlling pacing intervals based on a motion sensor signal for optimizing mechanical synchrony of heart chambers. The cardiac pacemaker may be a leadless pacemaker in some examples, implanted wholly within a heart chamber and is configured to sense cardiac events of at least two different heart chambers and may deliver pacing pulses to one or two different heart chambers. For example, the pacemaker may be configured to deliver dual chamber atrial and ventricular pacing, atrial synchronized single chamber ventricular pacing, or atrial synchronized biventricular pacing. The pacemaker determines a synchrony metric from a motion signal produced by a motion sensor included in the pacemaker. Based on the synchrony metric, the pacemaker adjusts a pacing interval, e.g., an AV pacing interval and/or an interventricular pacing interval (e.g., a right ventricle to left ventricle pacing interval or left ventricle to right ventricle pacing interval). The AV and/or interventricular pacing interval is adjusted to promote mechanical synchrony of the heart chambers when a ventricular pacing pulse is delivered at the adjusted AV pacing interval following a sensed or paced atrial event and/or when a ventricular pacing pulse is delivered at the adjusted interventricular pacing interval following a ventricular pacing pulse or sensed R-wave in the opposing ventricular chamber.

Figure 1:
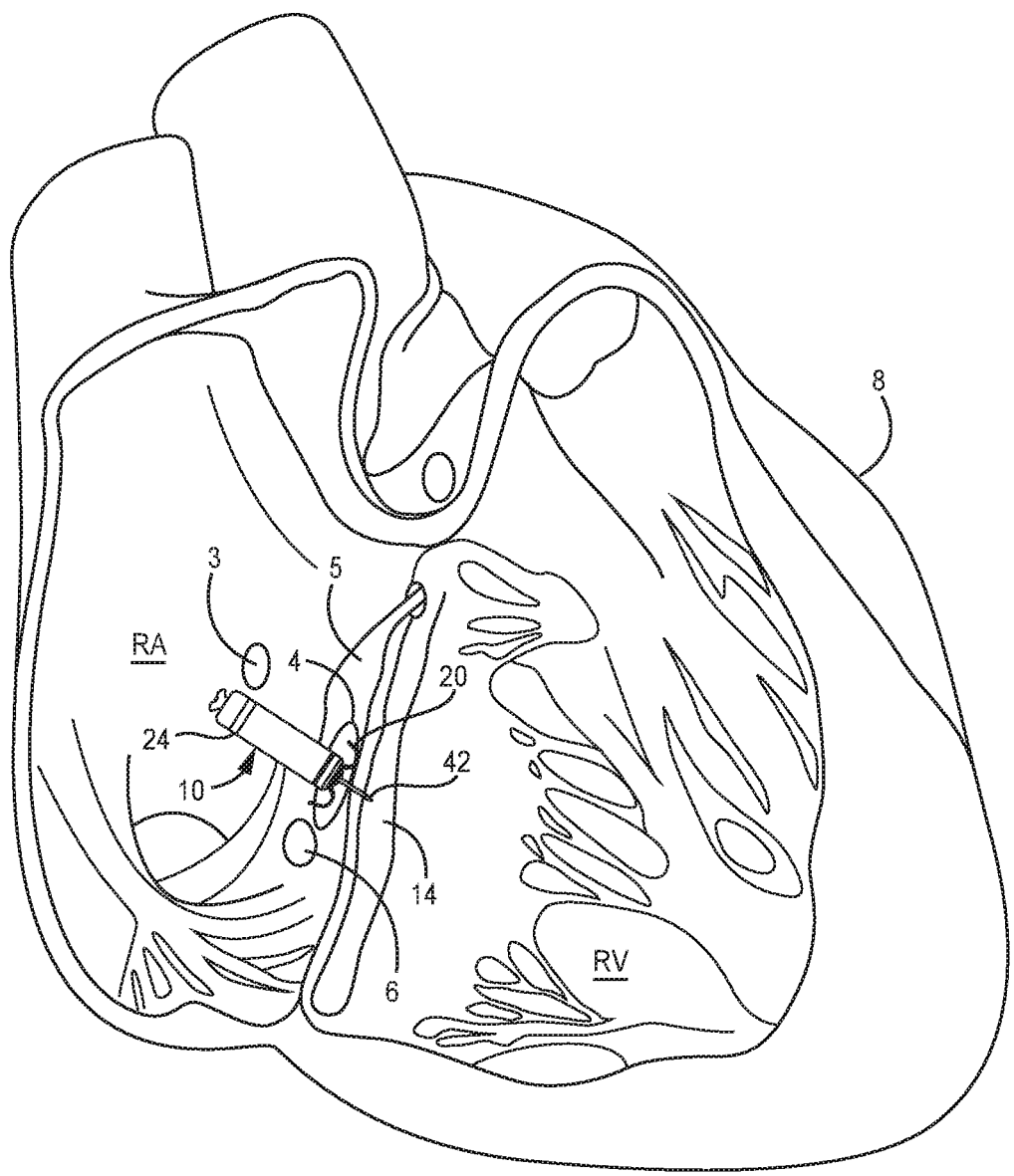
FIG. 1 is a conceptual diagram of an intracardiac pacemaker implanted in the right atrium of a patient's heart.

FIG. 1 is a conceptual diagram of a dual chamber intracardiac pacemaker 10 implanted in a patient's heart 8. Pacemaker 10 is shown implanted in the right atrium (RA) of the patient's heart 8 in a target implant region 4. Pacemaker 10 may include a fixation member 20 that anchors a distal end of the pacemaker 10 against the atrial endocardium in the target implant region 4. The target implant region 4 may lie between the Bundle of His 5 and the coronary sinus 6 and may be adjacent the tricuspid valve 3. Target implant region 4 may correspond or lie within the Triangle of Koch in some examples. Pacemaker 10 may be a leadless pacemaker including a distal ventricular electrode 42 extending away from the distal end of the pacemaker 10. When implanted in the target region 4, distal ventricular electrode 42 may extend through the atrial myocardium and the central fibrous body, and into the ventricular myocardium 14 or along the ventricular septum, without perforating entirely through the ventricular endocardial or epicardial surfaces. The distal ventricular electrode 42 may be carried at the distal end of a shaft extending from the pacemaker distal end for positioning the electrode 42 within the ventricular tissue for sensing ventricular signals, e.g., R-waves attendant to ventricular myocardial depolarizations, and delivering ventricular pacing pulses. In some examples, the distal ventricular electrode 42 is a cathode electrode provided for use in a bipolar pacing and sensing electrode pair with a housing-based anode electrode 24, located proximally along the pacemaker housing. As described below in conjunction with FIG. 2, pacemaker 10 may be a leadless dual chamber pacemaker including a distal housing-based electrode that can serve as an atrial cathode pacing and sensing electrode, paired with the housing-based proximal anode electrode 24. In this way, pacemaker 10 is capable of DDD pacing and sensing or CRT delivery.

While a particular implant region 4 is shown in FIG. 1 to enable an electrode to be positioned in the ventricular myocardium, it is recognized that a pacemaker configured to perform atrial synchronized ventricular pacing according to the techniques disclosed herein may be implanted at other locations for dual chamber pacing and sensing or single chamber ventricular pacing with dual chamber sensing, e.g., as described below in conjunction with FIG. 3.

The pacemaker 10 includes a motion sensor that produces a motion signal, e.g., an accelerometer producing an acceleration signal, correlated to motion imposed directly on pacemaker 10 by movement of the heart 8 and blood when pacemaker 10 is implanted wholly within a heart chamber. In other examples, pacemaker 10 may be implanted epicardially on the heart 8, and the motion sensor produces a motion signal due to motion of the heart imparting motion directly on the pacemaker 10. A synchrony metric may be determined from a motion signal corresponding to ventricular systole as an indication of the synchronization of the left and right ventricular chambers and/or synchronization of the atrial and ventricular chambers. Based on the synchrony metric, the AV pacing interval may be adjusted to alter the time delay from an atrial paced or sensed event to the ventricular pacing pulse in a manner that promotes optimized AV synchronization and/or ventricular synchrony.

Figure 2:
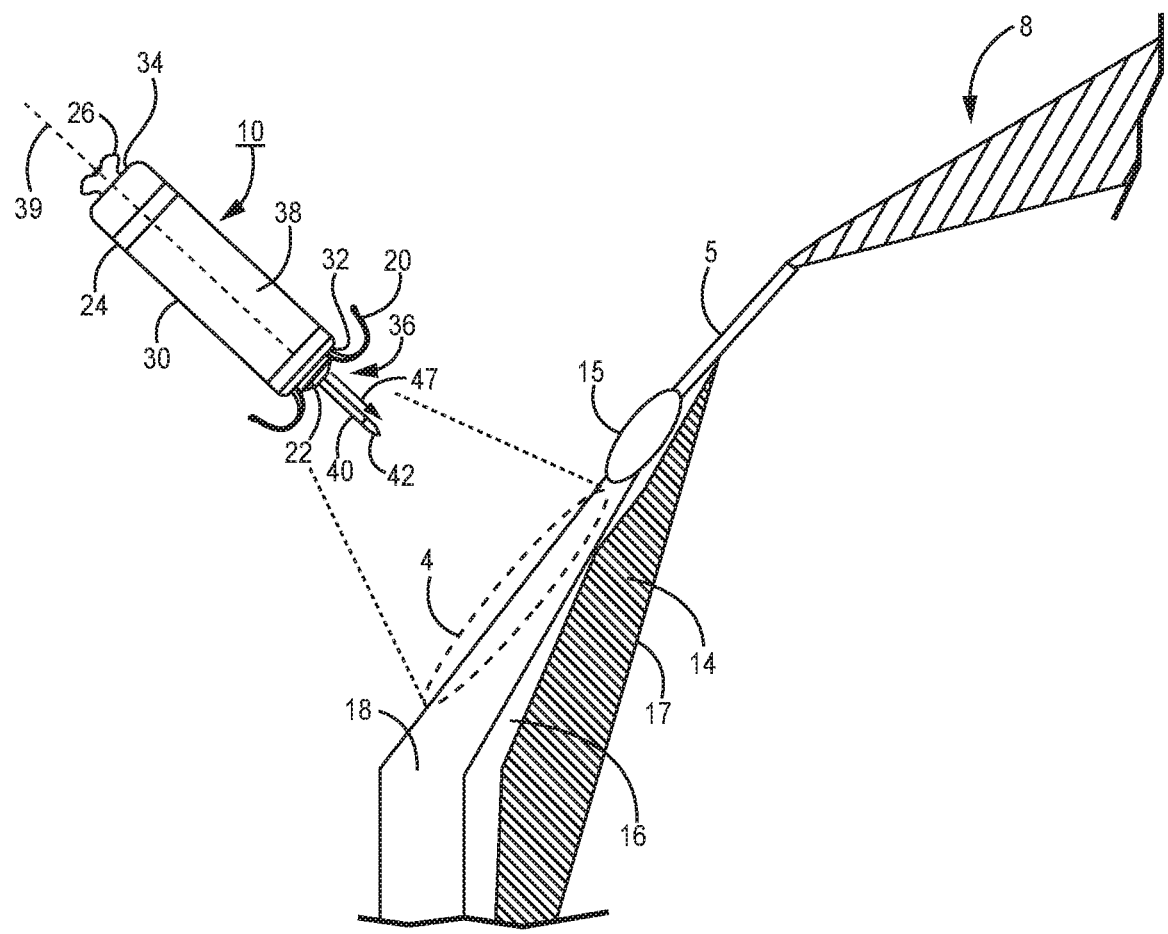
FIG. 2 is an enlarged conceptual diagram of the intracardiac pacemaker of FIG. 1.

FIG. 2 is an enlarged conceptual diagram of intracardiac pacemaker 10 and anatomical structures of the patient's heart 8. Intracardiac pacemaker 10 includes a housing 30 that defines a hermetically sealed internal cavity in which internal components of pacemaker 10 reside, such as a sensing circuit, therapy delivery circuit, control circuit, memory, telemetry circuit, a motion sensor, and a power source as generally described in conjunction with FIG. 4 below. The housing 30 may be formed from an electrically conductive material including titanium or titanium alloy, stainless steel, MP35N (a non-magnetic nickel-cobalt-chromium-molybdenum alloy), platinum alloy or other biocompatible metal or metal alloy. In other examples, housing 30 is formed from a non-conductive material including ceramic, glass, sapphire, silicone, polyurethane, epoxy, acetyl co-polymer plastics, polyether ether ketone (PEEK), a liquid crystal polymer, or other biocompatible polymer.

Housing 30 includes a longitudinal sidewall 38 that extends from pacemaker housing distal end 32 to pacemaker housing proximal end 34 and may be generally cylindrical, having a longitudinal axis 39, to facilitate catheter delivery to the target region 4. In other examples, however, housing 30 may be prismatic or other shapes and is not limited to the generally cylindrical example shown herein. Housing 30 may include a delivery tool interface member 26, e.g., at the proximal end 34, for engaging with a delivery tool during implantation of pacemaker 10.

A portion of housing 30 may function as an anode electrode during pacing and/or sensing. In the example shown, a housing-based electrode 24 is shown to circumscribe a proximal portion of longitudinal sidewall 38. When housing 30 is formed from an electrically conductive material, such as a titanium alloy or other examples listed above, portions of housing 30 may be electrically insulated by a non-conductive material, such as a coating of parylene, polyurethane, silicone, epoxy or other biocompatible polymer, leaving one or more discrete areas of conductive material exposed to define an electrode, e.g., proximal housing-based electrode 24. When housing 30 is formed from a non-conductive material, such as a ceramic, glass or polymer material, an electrically-conductive coating or layer, such as titanium, platinum, stainless steel, or alloys thereof, may be applied to one or more discrete areas of housing 30 to form a housing-based electrode, e.g., proximal housing-based electrode 24. In other examples, proximal housing-based electrode 24 may be a component, such as a ring electrode, that is mounted or assembled onto housing 30. Proximal housing-based electrode 24 may be electrically coupled to internal circuitry of pacemaker 10, e.g., via electrically-conductive housing 30 or an electrical conductor when housing 30 is a non-conductive material. In the example shown, proximal housing-based electrode 24 is located nearer to housing proximal end 34 than housing distal end 32 and is therefore referred to as a "proximal housing-based electrode" 24. In other examples, however, a housing-based electrode 24 may be located at other positions along housing 30, e.g., relatively more distally than the position shown or along the proximal end 34.

At distal end 32, pacemaker housing 30 may include a distal fixation and electrode assembly 36 including fixation member 20 and distal ventricular electrode 42 carried by shaft 40 extending distally away from housing distal end 32. Distal ventricular electrode 42 may be at or near the free, distal end of shaft 40. Distal ventricular electrode 42 may have a conical or hemi-spherical distal tip with a relatively narrow tip diameter, e.g., less than 1 mm, for penetrating into and through tissue layers without requiring a sharpened tip or needle-like tip having sharpened or beveled edges that might otherwise produce a cutting action that could lead to lateral displacement of the distal ventricular electrode 42 and undesired tissue trauma.

Shaft 40 may be a normally straight, rigid member in some examples capable of being advanced through tissue to position distal ventricular electrode 42 for pacing ventricular tissue. In other examples, shaft 40 is relatively stiff possessing limited flexibility in lateral directions. Shaft 40 may be non-rigid to allow some lateral flexing with heart motion. However, in a relaxed state, when not subjected to any external forces, shaft 40 maintains a straight position as shown to hold distal ventricular electrode 42 spaced apart from housing distal end 32. Distal ventricular 42 and shaft 40 are configured to pierce through one or more tissue layers to position distal ventricular electrode 42 within a desired tissue layer, e.g., the ventricular myocardium. As such, shaft 40 may have a height 47 corresponding to the expected ventricular pacing site depth and may have a relatively high compressive strength along its longitudinal axis to resist bending in a lateral or radial direction when a longitudinal axial force is applied against distal ventricular electrode 42 when pressed against the implant site, e.g., by applying longitudinal pushing force to the proximal end 34 of housing 30 to advance electrode 42 into the tissue within the target implant region 4. Shaft 40 may be longitudinally non-compressive. Shaft 40 may be elastically deformable in lateral or radial directions when subjected to lateral or radial forces to allow temporary flexing, e.g., with tissue motion, but returns to its normally straight position when lateral forces diminish.

Fixation member 20 may include one or more tines having a normally curved position. The tines of fixation member 20 may be held in a distally extended position within a delivery tool during implantation of pacemaker 10. The distal tips of the fixation member tines penetrate the heart tissue to a limited depth before elastically curving back proximally into the normally curved position (shown) upon release from the delivery tool. Aspects of fixation member 20 may correspond to the fixation member generally disclosed in U.S. Pat. No. 9,675,798 (Grubac, et al.) or in U.S. Pat. No. 9,119,959 (Rys et al.), both of which are incorporated herein by reference in their entirety.

In some examples, to provide dual chamber pacing and sensing, distal fixation and electrode assembly 36 includes a distal housing-based electrode 22 that can serve as a cathode electrode paired with proximal housing-based electrode 24. In the case of using pacemaker 10 for dual chamber pacing and sensing or CRT applications, distal ventricular electrode 42 may be used as a cathode electrode paired with proximal housing-based electrode 24 serving as a return anode electrode. Alternatively, distal housing-based electrode 22 may serve as a return anode electrode paired with distal ventricular electrode 42 for sensing ventricular signals and delivering ventricular pacing pulses. In other examples, distal housing-based electrode 22 may be a cathode electrode for sensing atrial signals and delivering pacing pulses to the atrial myocardium in the target implant region 4. When distal housing-based electrode 22 serves as an atrial cathode electrode, the proximal housing-based electrode 24 may serve as the return anode paired with distal ventricular electrode 42 for ventricular pacing and sensing and as the return anode paired with distal housing-based electrode 22 for atrial pacing and sensing. Distal housing-based electrode 22 is shown on the distal end 32 of pacemaker housing 30 and is coupled to an electrical feedthrough included in distal fixation and electrode assembly 36 for electrically coupling electrode 22 to pacing and sensing circuitry within housing 30. In other examples the distal housing-based electrode 22 may be positioned along a circumferential surface of the longitudinal sidewall 38.

As used herein, the term "housing-based" in reference to an electrode refers to an electrode that is carried directly on or coupled directly to a surface of the housing 30, which includes the exterior surfaces of the longitudinal sidewall 38 circumscribing the pacemaker 10 and the external faces of the proximal end 32 and distal end 34, without the use of a flexible elongated medical electrical lead. In contrast, a "lead-based" electrode is carried by a flexible lead body that encloses an electrical conductor (e.g., a wire or cable) that electrically couples the electrode to a proximal connector pin of the lead that is received by a connector assembly, sometimes referred to as a "header," for electrical connection to internal pacemaker circuitry. A housing-based electrode is not carried by an elongated, flexible lead body. Each of electrodes 22, 24 and 42 are "housing-based electrodes" in that pacemaker 10 is a leadless pacemaker with each electrode directly on or coupled directly to the pacemaker housing without the use of an elongated flexible lead body carrying a wire conductor that is manually connected to a pacemaker connector assembly.

In other examples, pacemaker 10 may be provided with four electrodes, one atrial sensing and pacing pair and one ventricular sensing and pacing pair. One or more ring, button or spherical electrodes, as examples, may be carried on distal end 32 to serve as an atrial cathode electrode paired with a relatively more proximal anode electrode. Various examples of electrode configurations that may be used for delivering atrial synchronized ventricular pacing from an intracardiac implant location of a pacemaker employing the techniques disclosed herein are generally disclosed in pre-grant U.S. Patent Publication No. 2019/0083779 (Yang, et al.) and pre-grant U.S. Patent Publication No. 2019/0083800 (Yang, et al.), both of which are incorporated herein by reference in their entirety. In other examples, the target pacing site may include the His bundle. An example intra-atrial pacemaker configured for pacing the ventricles via the His bundle from an atrial chamber implant site of the pacemaker is generally disclosed in pre-grant U.S. Patent Publication No. 2019/0134404 (Sheldon, et al.), incorporated herein by reference in its entirety.

As shown in FIG. 2, the target implant region 4 in some pacing applications is along the atrial endocardium 18, generally inferior to the AV node 15 and the His bundle 5. The shaft 40 and electrode 42 may be provided with a height 47 that penetrates through atrial endocardium 18 in the target implant region 4, through the central fibrous body 16 and into ventricular myocardium 14 without perforating through the ventricular endocardial surface 17. When the full height 47 of shaft 40 is fully advanced into the target implant region 4, distal ventricular electrode 42 rests within ventricular myocardium 14 and distal housing-based electrode 22 is positioned in intimate contact with, or close proximity to, atrial endocardium 18. Shaft 40 may have a total height 47 of approximately 3 mm to 8 mm in various examples. The diameter of shaft 40 may be less than 2 mm and may be 1 mm or less, or even 0.6 mm or less. In some examples, shaft 40 and electrode 42 may be provided with a tissue fixation feature such as a hook, helix, barb or other feature that tends to resist retraction of electrode 42 from the pacing site. For example, instead of a linear shaft 40 as shown, distal ventricular electrode 42 may be an exposed conductive tip of an insulated helical shaft that is advanced through the heart tissue from the atrial endocardium into ventricular myocardial tissue and/or proximate the His bundle for pacing the ventricles.

Figure 3:
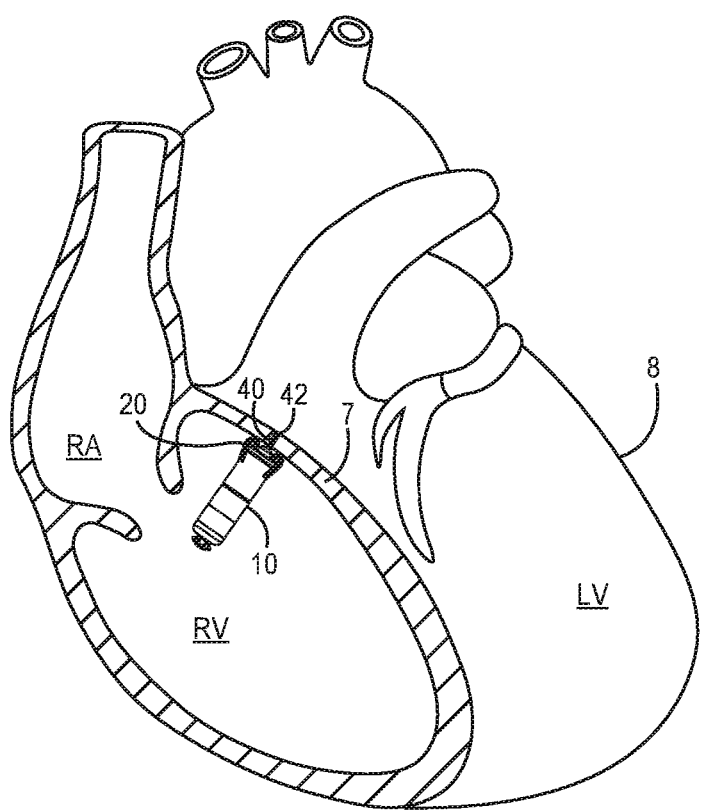
FIG. 3 is a conceptual diagram of an intracardiac pacemaker implanted in the right ventricle of a patient's heart.

FIG. 3 is a conceptual diagram of pacemaker 10 implanted at an alternative location for delivering atrial synchronized ventricular pacing according to another example. In some cases, pacemaker 10 may be implanted in a ventricular chamber and provided with distal ventricular electrode 42 positioned on a shaft extending away from the distal end of the pacemaker 10 to penetrate the ventricular septum 7. In the example shown in FIG. 3, pacemaker 10 is implanted in the right ventricle (RV) with the fixation member 20 anchored in the upper septal wall. Distal ventricular electrode 42 on shaft 40 is advanced through the septal wall 7, without puncturing through the left ventricular endocardial or epicardial surface, to position distal ventricular electrode 42 at a target ventricular pacing site in the left ventricle. The target ventricular pacing site may be in ventricular myocardium or along the ventricular conduction system, e.g., along a bundle branch. In some cases, the distal ventricular electrode 42 may be advanced into the septal wall 7 for placing the distal ventricular electrode 42 at a target pacing site for pacing the left ventricle (LV), e.g., along the left bundle branch, from a housing implant location within the RV. The distal housing-based electrode 22 may serve as a cathode electrode in operative proximity with the right ventricular myocardium for pacing the RV. Biventricular pacing may be provided by pacing the LV using the distal ventricular electrode 42 as a cathode electrode paired with housing-based proximal anode electrode 24 (see FIG. 2) and pacing the RV using the distal housing-based electrode 22 (see FIG. 2) paired with the housing-based proximal anode electrode 24. When pacemaker 10 is used for biventricular pacing, a synchrony metric may be determined from the motion sensor signal for optimizing the interventricular pacing interval between RV and LV pacing pulses and/or for optimizing an AV pacing interval between an atrial systolic mechanical event detected from the intraventricular motion signal and a ventricular pacing pulse.

As described herein, pacemaker 10 includes a motion sensor producing a cardiac mechanical signal including an atrial systolic event signal and ventricular mechanical event signals. The pacemaker 10, when placed in the RV, may or may not be able to sense atrial P-waves, attendant atrial depolarization, from the cardiac electrical signal sensed within the RV by pacemaker 10 because P-waves are relatively low amplitude signals compared to ventricular R-waves. As such, pacemaker 10 may sense an atrial systolic event by sensing the atrial systolic mechanical event signal from the motion signal for use in starting the AV interval for delivering atrial synchronized ventricular pacing. The RV or the LV may be paced at the AV interval. As disclosed herein, pacemaker 10 may determine a synchrony metric from the cardiac mechanical signal for optimizing the AV interval based on the synchrony metric, which may be correlated to ventricular mechanical synchrony. In some patients, mechanical synchrony of the ventricular chambers may become impaired, e.g., due cardiomyopathy, heart failure or conduction abnormalities. By controlling an AV interval used to deliver an LV pacing pulse synchronized to an atrial event, the timing of the RV contraction and the LV contraction may be resynchronized or ventricular dyssynchrony may at least be reduced.

Figure 4:
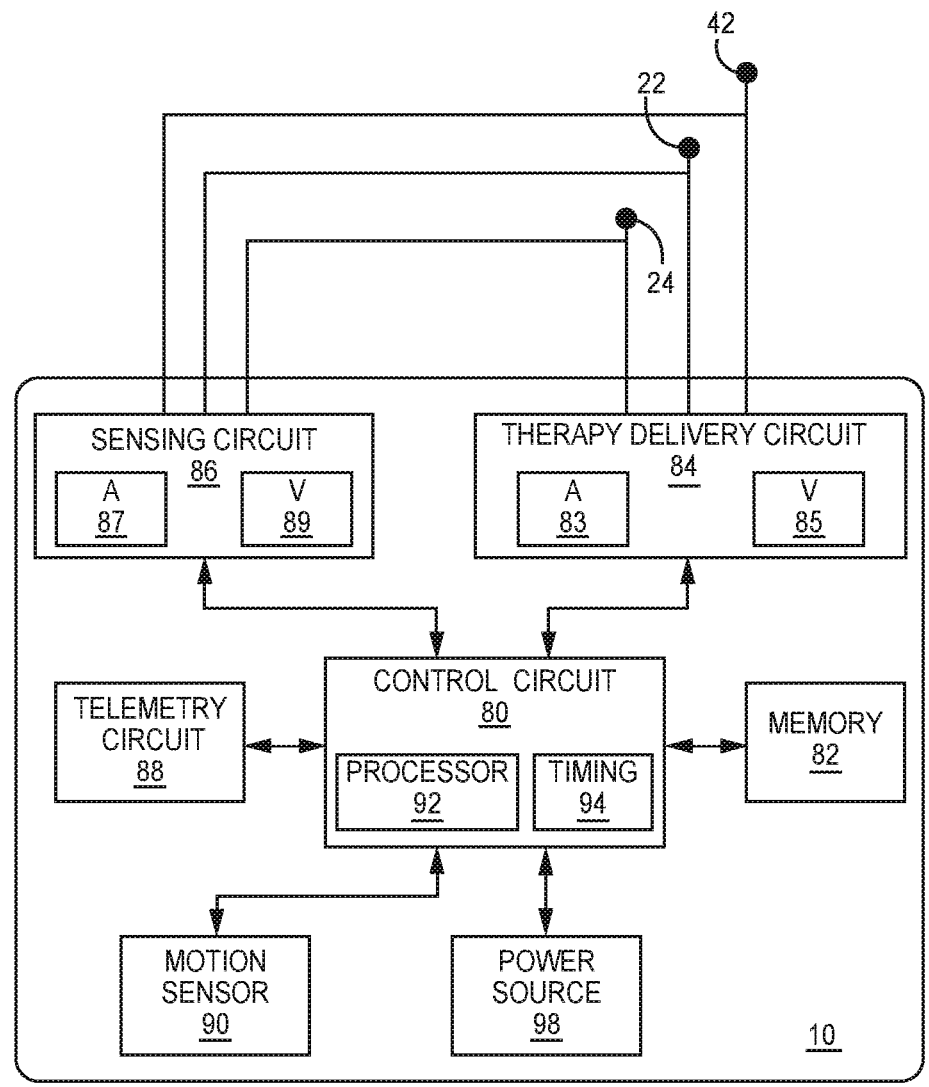
FIG. 4 is a block diagram of circuitry that may be enclosed within a pacemaker housing to provide the functions of cardiac pacing and sensing with pacing interval control based on a synchrony metric derived from a motion signal according to one example.

FIG. 4 is a block diagram of circuitry that may be enclosed within housing 30 of pacemaker 10 to provide the functions of cardiac pacing with pacing interval control based on a synchrony metric determined from an intracardiac motion signal according to one example. Pacemaker 10 may be configured for dual chamber pacing and sensing, e.g., in the implant location shown in FIG. 1, or single chamber ventricular pacing with dual chamber sensing, e.g., in either of the implant locations of FIG. 1 or FIG. 3, or biventricular pacing with dual chamber sensing, e.g., as shown in FIG. 3. The electronic circuitry enclosed within housing 30 includes software, firmware and hardware that cooperatively monitor atrial and ventricular cardiac signals, determine when a pacing therapy is necessary, and deliver electrical pacing pulses to the patient's heart as needed according to programmed pacing mode and pacing pulse control parameters. As disclosed herein, the circuitry further includes motion sensing capabilities for use in a pacing control feedback loop for adjusting the AV interval scheduled between atrial events and ventricular pacing pulses and/or an interventricular interval between right and left ventricular electrical events to promote optimal mechanical synchrony between heart chamber contractions. Synchrony between the atria and ventricles and synchrony between the RV and LV as well as coordinated contraction of regions of each ventricular chamber may be improved through the adjustment of the AV interval and/or the interventricular interval based on one or more synchrony metrics as disclosed herein. The electronic circuitry includes a control circuit 80, memory 82, therapy delivery circuit 84, sensing circuit 86, telemetry circuit 88 and motion sensor 90 for producing a signal that includes cardiac mechanical event signals correlated to cardiac motion.

A power source 98 provides power to the circuitry of pacemaker 10 including each of the components 80, 82, 84, 86, 88 and 90 as needed. Power source 98 may include one or more energy storage devices, such as one or more rechargeable or non-rechargeable batteries. The connections between power source 98 and each of the other components 80, 82, 84, 86, 88 and 90 are to be understood from the general block diagram of FIG. 4, but are not shown for the sake of clarity. For example, power source 98 is coupled to one or more charging circuits included in therapy delivery circuit 84 for providing the power needed to charge holding capacitors included in therapy delivery circuit 84 that are discharged at appropriate times under the control of control circuit 80 for delivering pacing pulses, e.g., according to a dual chamber pacing mode. Power source 98 is also coupled to components of sensing circuit 86, such as sense amplifiers, analog-to-digital converters, switching circuitry, etc., motion sensor 90, telemetry circuit 88 and memory 82 to provide power to the various circuits as needed.

The functional blocks shown in FIG. 4 represent functionality included in pacemaker 10 and may include any discrete and/or integrated electronic circuit components that implement analog and/or digital circuits capable of producing the functions attributed to pacemaker 10 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the pacemaker and by the particular detection and therapy delivery methodologies employed by the pacemaker. Providing software, hardware, and/or firmware to accomplish the described functionality in the context of any modern cardiac medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other circuits to perform the atrial synchronized ventricular pacing functions or other dual chamber sensing and pacing therapy delivery functions attributed herein to pacemaker 10. The non-transitory computer-readable media storing the instructions may include any of the media listed above.

Control circuit 80 communicates, e.g., via a data bus, with therapy delivery circuit 84 and sensing circuit 86 for sensing cardiac electrical signals and controlling delivery of cardiac electrical stimulation therapies in response to sensed cardiac events, e.g., P-waves and R-waves, or the absence thereof. Distal ventricular electrode 42, distal housing-based electrode 22, and proximal housing-based electrode 24 are electrically coupled to therapy delivery circuit 84 for delivering electrical stimulation pulses to the patient's heart and to sensing circuit 86 for sensing cardiac electrical signals.

Sensing circuit 86 receives cardiac electrical signals via electrodes 22, 24 and/or 42 and may include multiple sensing channels, e.g., an atrial (A) sensing channel 87 and a ventricular (V) sensing channel 89. Distal housing-based electrode 22 and proximal housing-based electrode 24 may be coupled to atrial sensing channel 87 for sensing atrial electrical event signals, e.g., P-waves attendant to the depolarization of the atrial myocardium. Distal ventricular electrode 42 and proximal housing-based electrode 24 (or distal housing-based electrode 22) may be coupled to ventricular sensing channel 89 as a ventricular sensing electrode pair for sensing ventricular electrical event signals, e.g., R-waves attendant to the depolarization of the ventricular myocardium. In examples that include additional electrodes carried by pacemaker housing 30 and/or shaft 40, sensing circuit 86 may include switching circuitry for selectively coupling an atrial sensing electrode pair to atrial sensing channel 87 and a ventricular sensing electrode pair to ventricular sensing channel 89. Switching circuitry may include a switch array, switch matrix, multiplexer, or any other type of switching device suitable to selectively couple components of sensing circuit 86 to selected electrodes.

Each of atrial sensing channel 87 and ventricular sensing channel 89 may include cardiac electrical event detection circuitry for detecting P-waves and R-waves, respectively, from the cardiac electrical signals received by the respective sensing channels. The cardiac electrical event detection circuitry included in each atrial and ventricular channel 87 and 89, respectively, may be configured to amplify, filter, digitize and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers or other analog or digital components. A cardiac event sensing threshold, e.g., a P-wave sensing threshold and an R-wave sensing threshold, may be automatically adjusted by each respective sensing channel 87 and 89 under the control of control circuit 80, e.g., based on timing intervals and sensing threshold values determined by control circuit 80, stored in memory 82, and/or controlled by hardware, firmware and/or software of control circuit 80 and/or sensing circuit 86. Sensing circuit 86 may apply various blanking and refractory periods to the received cardiac electrical signals to control sensing of atrial and ventricular events in a manner that avoids false or oversensing of atrial and ventricular electrical events.

Each channel 87 and 89 may be configured to produce a sensed event signal that is passed to control circuit 80 in response to a received cardiac electrical signal crossing a respective atrial P-wave sensing threshold or ventricular R-wave sensing threshold. For example, atrial sensing channel 87 may produce a P-wave sensed event signal in response to a P-wave sensing threshold crossing. Ventricular sensing channel 89 may produce an R-wave sensed event signal in response to an R-wave sensing threshold crossing. The sensed event signals are used by control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from atrial sensing channel 87 may cause control circuit 80 to inhibit a scheduled atrial pacing pulse (when pacemaker 10 is implanted within the RA) and schedule a ventricular pacing pulse at a programmed AV pacing interval. As described herein, the AV pacing interval between a sensed atrial P-wave and a ventricular pacing pulse may be adjusted based on analysis of a signal from motion sensor 90. If an R-wave is sensed before the AV pacing interval expires, the ventricular pacing pulse is inhibited. If the AV pacing interval expires before control circuit 80 receives an R-wave sensed event signal from ventricular sensing channel 89, control circuit 80 controls therapy delivery circuit 84 to deliver the scheduled ventricular pacing pulse synchronized to the sensed P-wave.

When positioned in the RA for dual chamber pacing and sensing, e.g., as in FIG. 1, control circuit 80 may set a lower pacing rate interval used to control delivery of atrial pacing pulses, e.g., by setting an AA pacing interval. When a P-wave sensed event signal is not received by control circuit 80 from atrial sensing channel 87 prior to expiration of the AA pacing interval, control circuit 80 controls therapy delivery circuit 84 to deliver an atrial pacing pulse and start an AV pacing interval. Control circuit 80 may set a VV pacing interval to control ventricular pacing at a minimum lower rate in the absence of a sensed atrial event that triggers a ventricular pacing pulse.

When configured for dual chamber pacing, therapy delivery circuit 84 may include an atrial pacing circuit 83 and a ventricular pacing circuit 85. Each pacing circuit 83 and 85 includes charging circuitry, one or more charge storage devices such as one or more low voltage holding capacitors, an output capacitor, and switching circuitry that controls when the holding capacitor(s) are charged and discharged across the output capacitor to deliver a pacing pulse to the pacing electrode vector coupled to the respective pacing circuit 83 or 85. Distal ventricular electrode 42 and proximal housing-based electrode 24 may be coupled to ventricular pacing circuit 85 as a bipolar cathode and anode pair for delivering ventricular pacing pulses, e.g., upon expiration of an AV or VV pacing interval set by control circuit 80 for providing atrial-synchronized ventricular pacing and a base lower ventricular pacing rate.

Atrial pacing circuit 83 may be coupled to distal housing-based electrode 22 and proximal housing-based electrode 24 to deliver atrial pacing pulses. Control circuit 80 may set atrial pacing intervals according to a programmed lower pacing rate or a temporary lower rate set according to a rate-responsive sensor indicated pacing rate. Atrial pacing circuit 83 is optional in some examples. For instance, some patients may have normal SA node and atrial electrical function but experience AV block or other ventricular conduction abnormalities or dyssynchrony providing an indication for ventricular pacing but not requiring atrial pacing. As such, pacemaker 10 may be configured for single chamber ventricular pacing and dual chamber sensing of both atrial and ventricular events. When atrial pacing circuit 83 is included, atrial pacing pulses may be delivered when a P-wave sensed event signal is not received from atrial sensing channel 87 prior to expiration of an AA pacing interval. Control circuit 80 starts an AV pacing interval in response to a delivered atrial pacing pulse to provide synchronized ventricular pacing. As described herein, the AV pacing interval between an atrial pacing pulse and a ventricular pacing pulse may be adjusted based on analysis of a signal from motion sensor 90.

In some examples, pacemaker 10 may be configured to deliver biventricular pacing, e.g., in the implant position of FIG. 3, in which case the atrial pacing channel 83 is not required. However, a right ventricular pacing channel and left ventricular pacing channel may be provided. For example, distal ventricular electrode 42 and proximal housing electrode 24 may be coupled to ventricular channel 85 to deliver left ventricular pacing pulses. Instead of an "atrial" pacing channel 83, the second pacing channel 83 may be a right ventricular pacing channel coupled to distal housing based electrode 22 and proximal housing based electrode 24 for delivering right ventricular pacing pulses. In this way, biventricular pacing may be delivered for providing CRT to improve or restore ventricular synchrony. The right and left ventricular pacing pulses may be delivered at an interventricular (V1-V2) pacing interval that controls the relative timing of electrical activation of the right and left ventricles. The interventricular interval may be adjusted based on a synchrony metric determined from an intraventricular motion signal received by control circuit 80 from motion sensor 90.

It is to be understood that an interventricular pacing interval may be a pacing interval that is used to control the time interval between a right ventricular sensed R-wave and a left ventricular pacing pulse, a left ventricular sensed R-wave and right ventricular pacing pulse, or between right and left ventricular pacing pulses. Each of these interventricular pacing intervals may set individually to different programmable settings and adjusted by control circuit 80 based on a synchrony metric determined from the intraventricular motion signal. Depending on individual patient need, the right ventricular electrical event may lead the left ventricular electrical event or vice versa. In the case of biventricular sensing and pacing, ventricular sensing channel 89 may include two ventricular sensing channels, one for sensing right ventricular R-waves, e.g., from electrodes 22 and 24, and one for sensing left ventricular R-waves, e.g., from electrodes 42 and 24.

Therapy delivery circuit 84 delivers pacing pulses by charging a holding capacitor of the respective atrial and ventricular pacing circuits 83 and 85 to a respective programmed pacing voltage amplitude and discharges the holding capacitor for a respective pacing pulse width according to control signals received from timing circuit 94 of control circuit 80. For example, timing circuit 94 may include programmable digital counters set by processor 92 of the control circuit 80 for controlling the basic pacing time intervals associated with various pacing modes. Control circuit 80 may also set the amplitude, pulse width, polarity or other characteristics of the cardiac pacing pulses generated by therapy delivery circuit 84, which may be based on programmed values stored in memory 82.

Pacemaker 10 includes a motion sensor 90 producing a signal that includes cardiac mechanical event signals that may be analyzed for use in controlling ventricular pacing delivered by therapy delivery circuit 84. Motion sensor 90 may be implemented as an accelerometer enclosed within housing 30 in some examples. In other examples, however, motion sensor may be another type of mechanical sensor, such as a pressure sensor, configured to produce an electrical signal correlated to mechanical motion imparted directly on the pacemaker housing 30 by the heart and blood when the pacemaker 10 is implanted within or on a heart chamber. Motion sensor 90 provides a signal to control circuit 80, e.g., to processor 92, for analysis for detecting cardiac mechanical events and determining a synchrony metric based on one or more aspects of one or more detected cardiac mechanical events. Based on the synchrony metric, control circuit 80 may set or adjust a pacing interval, e.g., either the AV interval used to control the timing of ventricular pacing pulses relative to atrial events, the interventricular interval used to control the timing between right and left ventricular electrical events, or both. The atrial event starting the AV interval may be an electrical event, e.g., a sensed P-wave or a delivered atrial pacing pulse, or a mechanical event sensed as an atrial systolic event from the motion signal produced by motion sensor 90. In the example of FIG. 3, for instance, control circuit 80 may be configured to sense mechanical atrial systolic events from the motion signal received from motion sensor 90 and start the AV interval in response to sensing the mechanical atrial systolic event.

The accelerometer of motion sensor 90 may be a one-, two- or three-dimensional accelerometer. For example, the accelerometer may include three single-axis accelerometer elements positioned orthogonally to one other to form three axes. Each axis of a single or multi-dimensional accelerometer included in motion sensor 90 may be defined by a piezoelectric element, micro-electrical mechanical system (MEMS) device or other sensor element capable of producing an electrical signal in response to changes in acceleration imparted on pacemaker 10 and subsequently the sensor element, e.g., by converting the acceleration to a force or displacement of the motion sensor element that is converted to the electrical signal by the motion sensor element.

Each motion sensor element produces an acceleration signal corresponding to a vector aligned with the axis of the sensor element. Each motion sensor element produces a DC component corresponding to the vector component of gravitational force along the respective motion sensor axis. Each motion sensor element produces an AC component correlated to the acceleration due to motion of the patient, along the respective axis. The AC acceleration signals produced by each axis of the motion sensor may include acceleration imposed directly on the housing 30 of pacemaker 10, causing acceleration of pacemaker housing 30, due to movement of blood within the RA when implanted in the RA or within the RV when implanted in the RV and acceleration due to heart chamber motion, e.g., atrial chamber contraction and relaxation and ventricular chamber contraction and relaxation. The acceleration signals may further include signals due to acceleration of pacemaker housing 30 caused by patient body motion, e.g., due to patient physical activity as the patient engages in activities of daily living, exercise, etc.

In some examples, the accelerometer may have one "longitudinal" axis that is parallel to or aligned with the longitudinal axis 39 (see FIG. 2) of pacemaker 10 and two orthogonal axes that extend in radial directions relative to the longitudinal axis 39, e.g., radially outward toward longitudinal sidewall 38. Although one axis or combination of axes may provide greater signal strength of cardiac mechanical events of interest the optimal axis (or axes) for sensing cardiac mechanical event signals may vary between motion sensor orientations, pacemaker orientation after implant and other factors. As such, practice of the techniques disclosed herein is not limited to a particular orientation of the motion sensor within or along housing 30 or relative to heart 8. In general, motion sensor 90 produces an intra-cardiac motion signal from at least one motion sensor signal axis from which control circuit 80 is configured to detect and analyze cardiac mechanical event signals for use in controlling pacing intervals used by therapy delivery circuit 84 during ventricular pacing. In the example of FIG. 1, the intra-cardiac motion signal is an intra-atrial motion signal including a mechanical atrial systolic event signal and mechanical ventricular systolic event signals. In the example of FIG. 3, the intra-cardiac motion signal is an intra-ventricular signal that also includes a mechanical atrial systolic event signal and mechanical ventricular systolic event signals. Control circuit 80 analyzes the intra-cardiac motion signal to detect cardiac mechanical events, determine a synchrony metric correlated to heart chamber synchrony, and adjusts the AV interval and/or interventricular interval based on the synchrony metric as needed to improve heart chamber synchrony.

As used herein, "heart chamber synchrony" may refer to the synchrony between the atrial contraction and subsequent ventricular contraction and/or the synchrony between concurrent right and left ventricular contractions. Heart chamber synchrony may further include synchrony between segments of a heart chamber, e.g., synchrony or coordination between the left ventricular apical, mid and basal segments of the anterior, septal and inferior walls. For example, mechanical synchrony between the atrial contraction and ventricular contraction may be considered to be "optimized" when the AV interval causes ventricular contraction to start no earlier than the end of the atrial contraction and/or when a synchrony metric correlated to ventricular contractility is maximized relative to other AV intervals. Mechanical synchrony between right and left ventricular contractions or segments thereof may be considered to be "optimized" when a synchrony metric indicates that the simultaneity of right and left ventricle contraction and relaxation is maximized. Examples of synchrony metrics that may be determined by control circuit 80 are described below in conjunction with FIG. 5.

In some examples, control circuit 80 may further analyze a motion signal received from motion sensor 90 for determining a metric of patient physical activity to provide rate responsive pacing. The patient physical activity metric, which may be correlated to a need for increased cardiac output or increased metabolic demand, determined from a motion sensor signal may be used by control circuit 80 to determine a sensor indicated pacing rate. Control circuit 80 may adjust a programmed base lower pacing rate to a temporary, higher pacing rate according to the sensor indicated pacing rate. For example, the programmed base lower pacing rate may be 40 to 60 pulses per minute. Control circuit 80 may increase the pacing rate according to the sensor indicated pacing rate, which may be determined using a transfer function that relates the patient activity metric to a target heart rate needed to support the indicated level of patient activity.

Pacemaker 10 may include a telemetry circuit 88 for communicating wirelessly with an external device, such as a programmer or home monitor. Telemetry circuit 88 may be configured to establish a communication link with an external device using a radio frequency (RF) link such as BLUETOOTH®, Wi-Fi, Medical Implant Communication Service (MICS) or other communication bandwidth. For example, telemetry circuit 88 may be configured for communication with an external programmer or monitor such as the CARELINK® Programmer or MYCARELINK® Patient Monitor, both available from Medtronic, Inc. Minneapolis Minn., USA. Control parameters utilized by control circuit 80 for sensing cardiac events, and controlling pacing therapy delivery may be programmed into memory 82 via telemetry circuit 88. Telemetry circuit 88 includes a transceiver and antenna for communicating with an external device according to an implemented communication protocol. Under the control of control circuit 80, telemetry circuit 88 may receive downlink telemetry from and send uplink telemetry to the external device. In some cases, telemetry circuit 88 may be used to transmit and receive communication signals to/from another medical device implanted in the patient.

Figure 5:
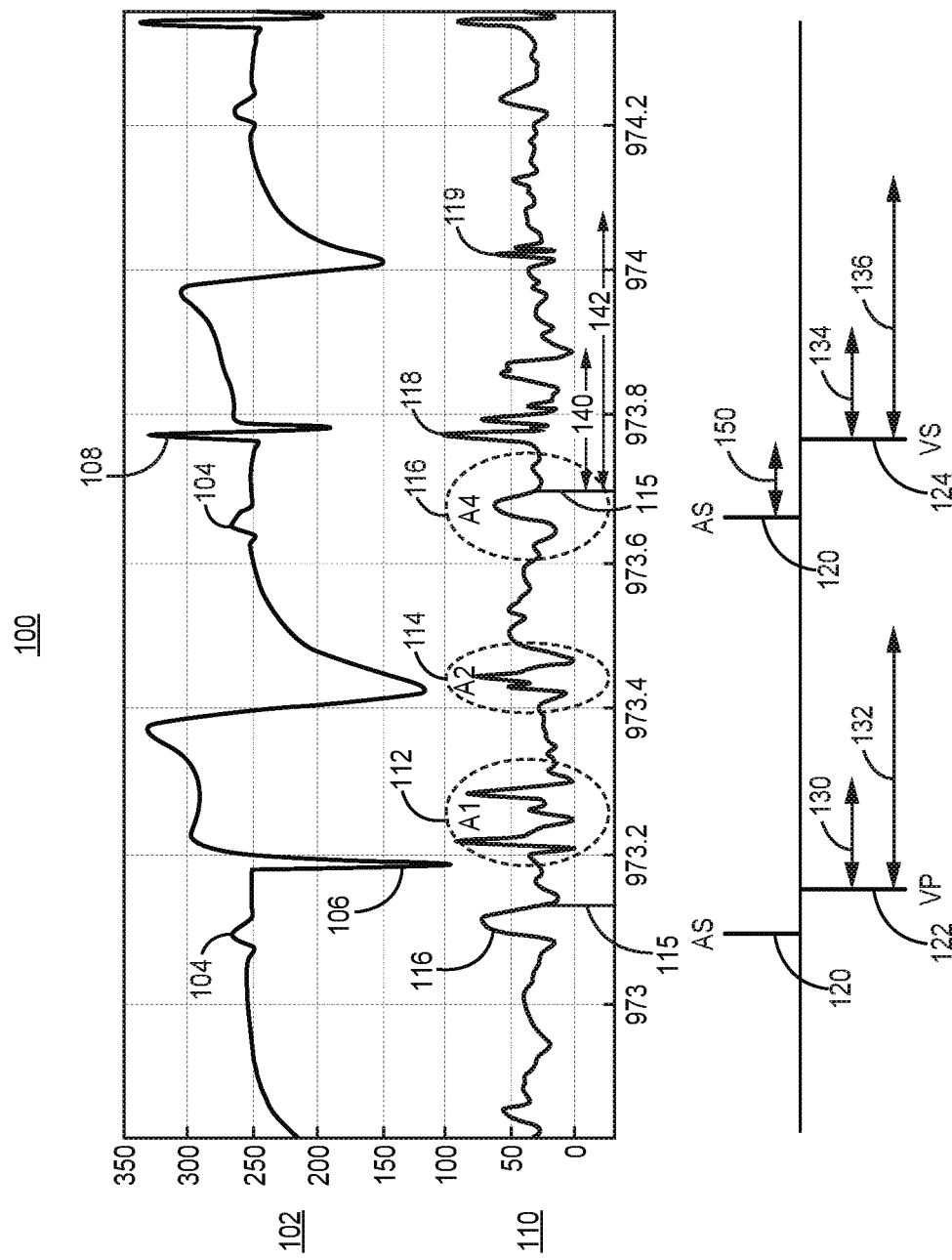
FIG. 5 is a diagram of cardiac signals that may be produced by the pacemaker of FIG. 1, including atrial and ventricular electrical and mechanical events.

FIG. 5 is a diagram 100 of cardiac signals that may be produced by pacemaker 10 including atrial and ventricular electrical and mechanical event signals that may be detected by control circuit 80 for use in determining a synchrony metric. The synchrony metric may be correlated to mechanical synchrony or contractility of the heart chambers. Control circuit 80 may adjust the AV pacing interval and/or inter-ventricular pacing interval based on one or more determined synchrony metrics to promote heart chamber synchronization and/or improved contractility. The synchrony metric is determined by detecting one or more mechanical events from the motion sensor signal received from motion sensor 90 and determining a metric or feature based on the detected mechanical events.

In FIG. 5, a cardiac electrogram (EGM) signal 102 and a motion signal 110 that may be produced by sensing circuit 86 and motion sensor 90, respectively, are shown. EGM signal 102 may be produced from a cardiac electrical signal received by pacemaker 10, e.g., via electrodes 42 and 24. In this example, motion signal 110 is an acceleration signal produced by the motion sensor 90 when pacemaker 10 is implanted wholly within the right atrial chamber. Motion signal 110 may be referred to as an intra-atrial motion signal.

EGM signal 102 includes P-waves 104 attendant to the depolarization of the atrial myocardium. The atrial sensing channel 87 of sensing circuit 86 may be configured to produce an atrial sensed event signal 120 that is passed to control circuit 80 to indicate that the P-wave 104 has been sensed. An atrial systolic event, labeled A4 signal 116, in motion signal 110 follows each P-wave 104 and represents the mechanical contraction of the atrium. The A4 signal 116 is also referred to herein as a "mechanical atrial systolic event."

EGM signal 102 includes a paced R-wave signal 106 and an intrinsic R-wave signal 108, each attendant to depolarization of the ventricular myocardium. Each R-wave 106 and 108 is followed by a respective A1 signal 112 and 118 of motion signal 110. The A1 signals 112 and 118 occur with ventricular contraction following the electrical depolarization and may correspond to the onset of ventricular mechanical systole. The A1 signals 112 and 118 are each followed by a respective A2 signal 114 and 119 which may occur with closure of the aortic and pulmonic valves, marking the approximate offset or end of ventricular mechanical systole (and onset of ventricular mechanical diastole). Both the A1 signals (112 and 118) and the A2 signals (114 and 119) are referred to herein as "ventricular systolic event signals" because the A1 signal marks the onset of mechanical systole and the A2 signal marks the end of mechanical systole of the ventricles.

A time relationship between an electrical event of EGM signal 102 and a mechanical event of motion signal 110 and/or a time relationship between two mechanical events of motion signal 110 may be determined in some examples as a synchrony metric used in setting and adjusting a pacing interval used to control the timing of ventricular pacing pulses delivered by pacemaker 10. Examples of various synchrony metrics that may be determined and used by control circuit 80 are described below. In order to determine such synchrony metrics, control circuit 80 detects the motion signal events, e.g., A1 signals, A2 signals, and/or A4 signals. In order to detect a desired mechanical event from motion signal 110, control circuit 80 may set various time windows and/or thresholds or other detection criteria for detecting the A1, A2 and A4 signals.

For example, the A4 signal 116 may be detected by setting an A4 window 150 following an atrial sensed event signal 120 received from sensing circuit 86. The A4 signal 116 may be detected in response to an A4 amplitude sensing threshold crossing during the A4 window 150. The A4 window 150 may expire upon a predetermined interval of time or upon receiving a ventricular sensed event signal 124 (or delivery of a ventricular pacing pulse 122). After detecting the A4 signal 116 in response to a threshold crossing, control circuit 80 may detect the peak amplitude, a negative peak slope, a return to baseline or A4 signal end 115 or other feature of the A4 signal 116 in order to identify a signal sample time point used for determining a synchrony metric as a time interval, e.g., a time interval from the A4 signal end 115 to immediately following A1 signal 112 or 118. In other examples, the A4 window 150 may be set relative to ventricular events, e.g., after a post-ventricular atrial refractory period following ventricular pacing pulse 122 or ventricular sensed event signal 124.

An A1 window 130 may be set following a ventricular pacing pulse 122 for detecting the paced A1 signal 112 based on an A1 amplitude threshold crossing by motion signal 110 during the A1 window 130 in some examples. Similarly, an A1 window 134 may be set following a ventricular sensed event signal 124 for detecting the intrinsic A1 signal 118. The A1 windows 130 and 134 may have the same duration or different durations due to any difference in the timing of the mechanical contraction following a ventricular pacing pulse compared to following an intrinsic R-wave. As shown in FIG. 5, the A1 signals 112 and 118 may have a double peak in some instances. The intra-atrial or inter-ventricular A1 signal may include two or more peaks due to ventricular dyssynchrony between the right and left ventricles and/or regional dyssynchrony of the segments of a ventricle. The intra-cardiac (or an epicardial motion signal) may be more sensitive to regional or segmental and/or inter-ventricular dyssynchrony, resulting in a multi-peak A1 signal, than other types of sensor signals sensed further away from the heart, which provide a more global signal of cardiac electrical and/or mechanical events. The time of a feature of the A1 signal, e.g., the first peak, the second peak, a maximum peak, a maximum slope or other feature, may be identified by control circuit 80 for use in determining the synchrony metric as a time interval beginning or ending with the A1 signal 112. In other examples, a synchrony metric may be determined as a feature of the A1 signal, e.g., a maximum peak amplitude, a signal width, maximum slope number of peaks, or other feature that may be indicative of ventricular synchrony or contractility.

Control circuit 80 may set an A2 window 132 following a ventricular pacing pulse 122 and an A2 window 136 following ventricular sensed event signal 124 to facilitate detection of the A2 signals 114 and 119, respectively. The A2 windows 132 and 136 may have the same or different durations since the timing of the A2 signal 119 following an intrinsic R-wave 108 may be different than the timing of the A2 signal 114 following a ventricular pacing pulse 122. The A2 signals 114 and 119 may be detected during the respective A2 windows 132 and 136, after the respective A1 windows 130 and 134 expire or after the respective A1 signals 112 and 118 have been detected. The time of detecting the A2 signal in response to a threshold amplitude crossing by motion signal 110 and/or the time of a feature of the A2 signal 114 or 119 identified by control circuit 80, e.g. the maximum peak amplitude, maximum slope (or derivative), number of peaks, or signal width, may be determined for use in determining a synchrony metric.

In other examples, detection of the end 115 of the A4 signal 116 may be used to set an A1 time window 140 and/or A2 time window 142 to facilitate detection of the ventricular mechanical event signals 112, 114, 118 or 119 following the end of the A4 signal 116. FIG. 5 depicts various examples of sensing windows that may be used to facilitate detection of cardiac mechanical events from motion signal 110. It is understood that mechanical event sensing control parameters including sensing threshold amplitudes and sensing windows may be set according to individual patient need. Various sensing windows for facilitating detection of a particular cardiac mechanical event may be defined relative to preceding electrical or mechanical events identified by control circuit 80.

Figure 6:
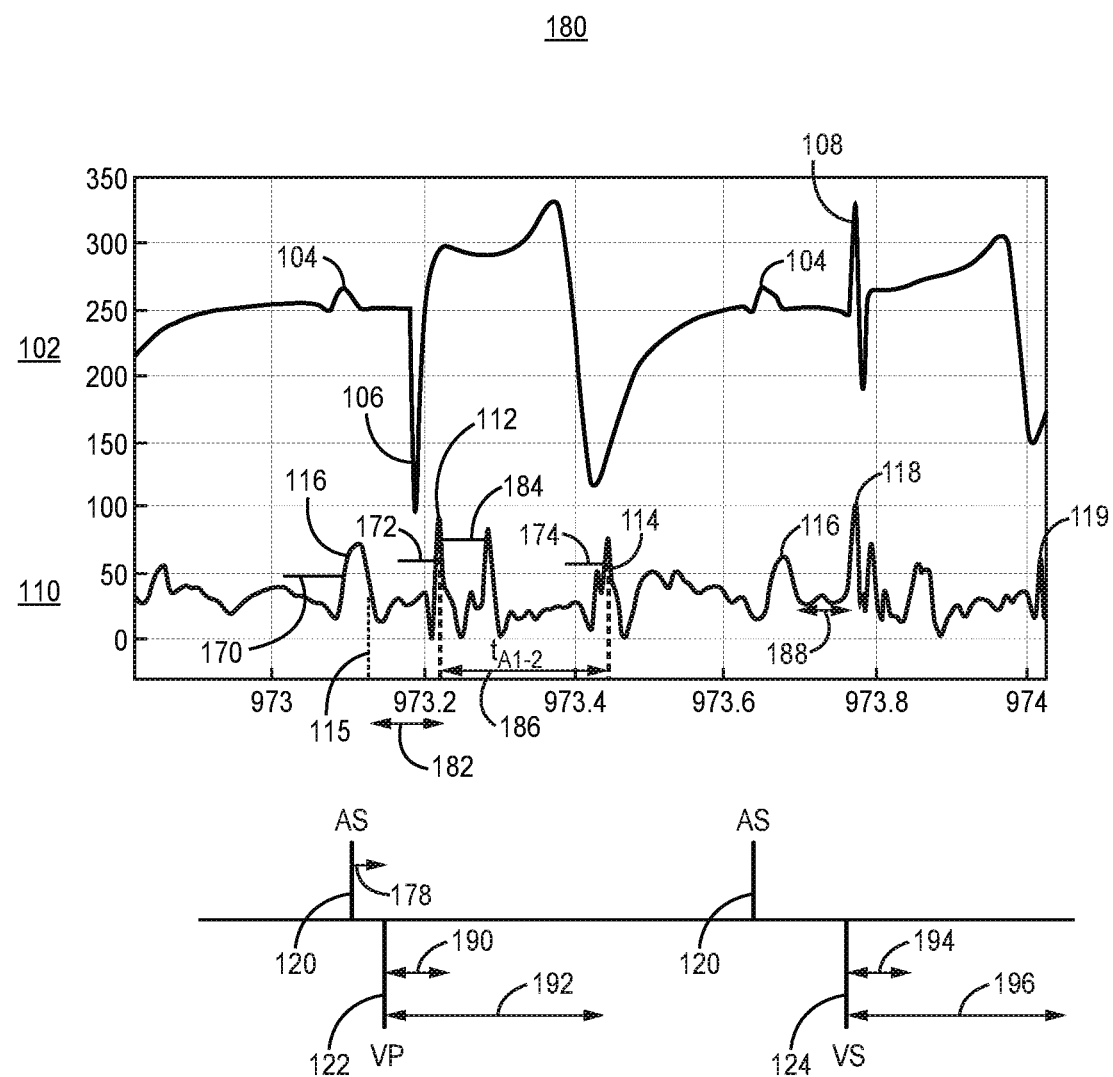
FIG. 6 is a diagram of the cardiac signals of FIG. 5 depicting various examples of synchrony metrics that may be determined by the pacemaker for controlling the AV interval.

FIG. 6 is a diagram 180 of the EGM signal 102 and motion signal 110 of FIG. 5 showing various examples of synchrony metrics that may be determined by control circuit 80 using motion signal 110. Various time intervals beginning and/or ending with a cardiac mechanical event detected from motion signal 110 or cardiac mechanical event signal features may be determined by control circuit 80 as a synchrony metric. Different synchrony metrics may be determined for use in setting and adjusting the AV interval for controlling atrial synchronized ventricular pacing and/or setting an interventricular interval depending on the clinical application. In some examples, the timing of the A4 signal 116, in particular the end 115 of the A4 signal 116, relative to the ventricular pacing pulse 122 or the A1 signal 112 may be determined as a synchrony metric. The onset of ventricular contraction should occur after atrial contraction is complete to avoid incomplete ventricular filling during atrial systole and to avoid ventricular contraction against a still-contracting atrial chamber. Accordingly, control circuit 80 may determine an A4-A1 time interval 182 from a fiducial point of the A4 signal 116 to a fiducial point of the A1 signal 112 as a synchrony metric. The fiducial point of the A4 signal 116 may be the time that the A4 event is detected based on the motion signal crossing an A4 sensing threshold amplitude 170, a maximum peak amplitude of the A4 signal 116, the ending time 115 of the A4 signal 116, a maximum negative slope of the A4 signal or other fiducial point identified by control circuit 80 as reference time point of atrial mechanical systole. The fiducial point of the A1 signal 112 may be the time that the A1 event is detected based on the motion signal crossing an A1 sensing threshold amplitude 172, a maximum peak amplitude of the A1 signal 116, a maximum positive slope of the A1 signal or other fiducial point identified by control circuit 80 as a reference time point of the onset of ventricular mechanical systole. If the A4-A1 time interval 182 is less than (or greater than) a threshold interval (or outside a target range), the AV pacing interval 178 started in response to an atrial sensed event signal 120 may be adjusted until the A4-A1 time interval falls within a target range or is at least longer than a minimum A4-A1 time interval threshold.

In some examples, a target synchrony metric value may be determined during non-paced, intrinsic ventricular heart beats. For instance, in a patient receiving bradycardia ventricular pacing for treating intermittent AV conduction block, a synchrony metric may be determined and used for setting the target synchrony metric value or range that is desired when ventricular pacing pulses are delivered in the absence of intrinsic R-waves. A patient experiencing intermittent AV block may have normal conduction intermittently that results in normal synchrony between the atria and ventricles and between the right and left ventricles. An intrinsic A4-A1 time interval 188 may be determined between an A4 signal 116 that is followed by a ventricular sensed event signal 124 and the subsequent A1 signal 118. The intrinsic A4-A1 time interval 188 may be used as a target A4-A1 time interval during ventricular pacing. When the A4-A1 interval 182 during ventricular pacing is shorter than the intrinsic A4-A1 time interval 188 or percentage thereof, control circuit 80 may increase the AV interval 178. When the paced A4-A1 interval 182 is longer than the intrinsic A4-A1 interval 188 or percentage thereof, control circuit 80 may decrease AV interval 178. When the A4-A1 interval 182 during ventricular pacing is within a threshold or target range of the intrinsic A4-A1 interval 188, control circuit 80 may leave the AV interval 178 unchanged. It is recognized that in some examples, a target A4-A1 interval based on the intrinsic A4-A1 interval 188 may be determined for multiple different atrial rates so that the AV interval 178 may be adjusted according to a target A4-A1 interval for a given heart rate or heart rate range.

In other examples, the patient may experience conduction delays during intrinsic AV conduction or may experience complete AV conduction block such that an intrinsic A4-A1 time interval is not useful or cannot be determined for use in setting a target value of the A4-A1 time interval used as a synchrony metric during ventricular pacing. In such cases, the target A4-A1 interval may be set based on empirical data, or established during other AV interval optimization studies performed on the patient, e.g., using echocardiography or other hemodynamic assessments or measurements for determining an optimized AV interval 178. When the AV interval 178 is deemed optimal for a given patient based on echocardiography or other clinical hemodynamic assessments, the optimized A4-A1 interval may be determined from the motion signal 110 and used as a target A4-A1 interval in adjusting the AV pacing interval 178.

Other synchrony metrics may be determined from motion signal 110 that may be used in addition to or alternatively to the A4-A1 time interval for adjusting a pacing interval. Other synchrony metric time intervals that may be determined by control circuit 80 include an A1 width interval 184 and/or an A1-A2 interval 186. The A1 width interval 184 may be the time interval between two separate peaks of a double-peaked A1 signal, as in the example of the A1 signal 112. The A1 width interval between two peaks of the A1 signal 112 may be correlated to synchrony between the RV and LV (or segments thereof) where one peak may correspond to right ventricular contraction and the other peak may correspond to left ventricular contraction. In other examples, the A1 width may be the width of a single-peaked A1 signal, e.g., at a predefined threshold amplitude. A relatively long A1 width interval 184 may indicate increased ventricular dyssynchrony. The AV interval 178 may be adjusted until the A1 width interval 184 is minimized or until the A1 signal 112 is reduced from two peaks to a single peak, indicating improved ventricular synchrony. Improved ventricular synchrony may include an improvement in the concurrent, synchronized contraction of the right and left ventricles and/or an improvement in the coordinated contraction of segments of one of the left or right ventricles. For example, in some patients, contraction of a portion of the ventricular wall of one ventricular chamber, either the right or left ventricle, may be delayed compared to other portions or segments of the ventricular chamber. To illustrate, contraction of the left ventricular lateral wall may be delayed compared to other portions of the left ventricle. A synchrony metric corresponding to improved ventricular synchrony between ventricular segments may correspond to a correction or reduction of regional or segmental contraction delays of a ventricular chamber.

Another example synchrony metric is the A1-A2 interval 186 determined between fiducial points of the A1 signal 112 and the A2 signal 184. For instance, the A1-A2 interval 186 may be determined between a crossing of the A1 sensing threshold 172 by motion signal 110 and a crossing of the A2 sensing threshold 174 by motion signal 110. Alternatively, the A1-A2 time interval 186 may be determined as the time interval between the maximum peak of the A1 signal 112 and the maximum peak of the A2 signal 116 or between another combination of a fiducial point of the A1 signal 112 and a fiducial point of the A2 signal 116 defining an A1-A2 interval. The A1-A2 interval 186 may be correlated to the ventricular systolic time interval or ejection phase and may be an indicator of ventricular synchrony. The A1 width 184 and/or A1-A2 interval 186 may be determined during ventricular pacing and compared to a respective target width and target A1-A2 interval. The target A1 width and the target A1-A2 interval may be based on an intrinsic A1 width and intrinsic A1-A2 interval, respectively, determined during non-paced ventricular beats or an A1 width and A1-A2 interval determined during other pacing interval optimization procedures such as echocardiography, etc.

In other examples, the synchrony metric may be determined as a time interval between a cardiac electrical event, intrinsically sensed or paced, and a cardiac mechanical event. For instance a Vpace-A1 time interval 190 may be determined as the time interval from the ventricular pacing pulse 122 to the maximum peak amplitude or other fiducial point of the A1 signal 112. A Vpace-A2 time interval 192 may be determined as the time interval from the ventricular pacing pulse 122 to the maximum peak amplitude or other fiducial point of the A2 signal 116. When the Vpace-A1 or Vpace-A2 time intervals 190 or 192 are used as a synchrony metric, a target range or threshold of the synchrony metric may be set based on a respective intrinsic Vsense-A1 time interval 194 or intrinsic Vsense-A2 time interval 196 determined during non-paced ventricular beats in some examples.

The synchrony metric is not limited to being determined as a time interval. In other examples, the synchrony metric may be determined as a feature of the A1 and/or A2 signals. In some examples, the control circuit 80 may set the A1 window 130 and/or A2 window 132 (see FIG. 5) and identify motion signal sample points that are greater than a predetermined threshold amplitude during the A1 window 130 and/or A2 window 132. The synchrony metric may be determined from the identified sample points, which may include integrating or summing the sample points, counting the sample points, determining a slope from the identified sample points, or determining the maximum peak amplitude from the identified sample points, as examples. The identified sample points may include sample points from one or both of the A1 and A2 signals 112 and 114. For instance, the area of the A1 signal 112 greater than a predetermined baseline or threshold amplitude may be determined by an integrator or summing circuit included in control circuit 80 and may be in indicator of ventricular synchrony. As the A1 signal area increases, greater ventricular dyssynchrony, between the right and left ventricles and/or between regions of one ventricular chamber, may be occurring. The AV interval 182 may be adjusted (increased or decreased) until the A1 signal area is either minimized (reaches a minimum value for all AV intervals tested) or falls within a target range or below a target threshold based on a target A1 signal area.

In another example, the number of sample points of the A1 signal and/or A2 signal that are greater than a predetermined threshold amplitude and within the A1 window 130, within both the A1 window 130 and the A2 window 132, or within the A2 window 130 but not the A1 window 130 may be counted (the A1 and A2 windows 130 and 132 are shown in FIG. 5). The synchrony metric may be determined as the number of sample points greater than the predetermined threshold. A relatively higher sample point count may be correlated to greater ventricular dyssynchrony. A sample point count may be determined by firmware or software of processor 92 or by a comparator and counter implemented in hardware of control circuit 80.

In still other examples, the area of the motion signal 110 within the A1 window 130, the area of the motion signal within the A2 window 132, the maximum peak amplitude of the A1 signal 112, the maximum peak amplitude of the A2 signal 114, the maximum slope (positive or negative) of the A1 signal 112, a maximum slope (positive or negative) of the A2 signal 114, or any combination thereof may be determined as synchrony metric(s) used for controlling adjustments to the AV interval 182 (or an interventricular interval) in a manner that promotes normal or improved heart chamber synchrony. Another example synchrony metric may be determined as a metric of variability of the motion signal 110 within the A1 and/or A2 window 130 and 132. For example, the number of inflection points or number of threshold crossings may indicate variation of the motion signal correlated to ventricular synchrony. The higher the number of inflection points or the higher the number of threshold crossings during the A1 and/or A2 window may be evidence of increased ventricular dyssynchrony. A pacing interval controlling the timing of ventricular pacing pulse delivery may be adjusted to reduce the number of inflection points or number of threshold crossings within the A1 and/or A2 window.

In some patients, such as a patient diagnosed with heart failure, ventricular pacing may be delivered by pacemaker 10 for providing CRT for improving ventricular synchrony. As such, a synchrony metric determined from the A1 signal 112 and/or A2 signal 114 correlated to ventricular synchrony may be determined. The AV interval 178 may be adjusted until the synchrony metric indicates improved ventricular synchrony, which may be an increase or decrease of the synchrony metric value depending on what synchrony metric is being determined. Since intrinsic AV conduction and conduction through the intrinsic ventricular conduction system, if present, may be abnormal or delayed, the target value for a synchrony metric may be determined based on empirical data or determined from motion signal 110 when the AV interval is deemed optimal based on other clinical measurements or assessments, such as an echocardiography study. When pacemaker 10 is implanted in the RV, the AV interval and/or the interventricular interval may be adjusted until the synchrony metric indicates improved ventricular synchrony.

In the examples of FIGS. 4 and 5, the atrial electrical events shown in EGM signal 102 are intrinsic atrial sensed events, e.g., P-waves sensed by atrial channel 87 of sensing circuit 86. It is to be understood, however, that an atrial electrical event used in setting an A4 window 150 and triggering the start of AV interval 178 may be an atrial pacing pulse delivered by pacemaker 10. The patient may be pacemaker dependent requiring atrial pacing on a chronic basis. In some cases, atrial pacing pulses are delivered in response to an absence of sensed P-waves or at a sensor indicated pacing rate to provide rate responsive pacing. The AV interval following an atrial pacing pulse may be set to a different interval than the AV interval set following an atrial sensed event signal. However in both cases, the AV interval may be adjusted based on a synchrony metric to promote optimized heart chamber synchronization. The target value or range of the synchrony metric may be the same value during atrial sensing and atrial pacing since the target value indicates an optimized or improved synchrony of the mechanical function of the heart chambers. In other examples, target values or ranges of a synchrony metric may be defined differently for use in adjusting the AV interval used during atrial sensing than the target value or range of the synchrony metric used for adjusting the AV interval used during atrial pacing. The heart's contractile responses during atrial pacing and during atrial sensing may differ. As such, different synchrony metric target values or ranges may indicate optimized heart chamber synchrony during atrial sensing and during atrial pacing. Furthermore, a different synchrony metric may be determined during atrial sensing for use in adjusting the sense-AV interval than the synchrony metric determined during atrial pacing used in adjusting the pace-AV interval.

In some examples, the atrial event that starts the AV pacing interval is the sensed A4 signal 116. In the example of FIG. 3, when the pacemaker 10 is implanted in a ventricular chamber, control circuit 80 may be configured to detect the A4 signal 116 and start the AV pacing interval. In this case, the AV pacing interval is set relatively short compared to the AV pacing interval 178 started in response to atrial sensed event signal 120 since the ventricular contraction should start upon or soon after atrial contraction is completed. In both cases, however, the AV pacing interval may be adjusted based on a synchrony metric determined following delivery of a ventricular pacing pulse and an established target value of the synchrony metric.

Figure 7:
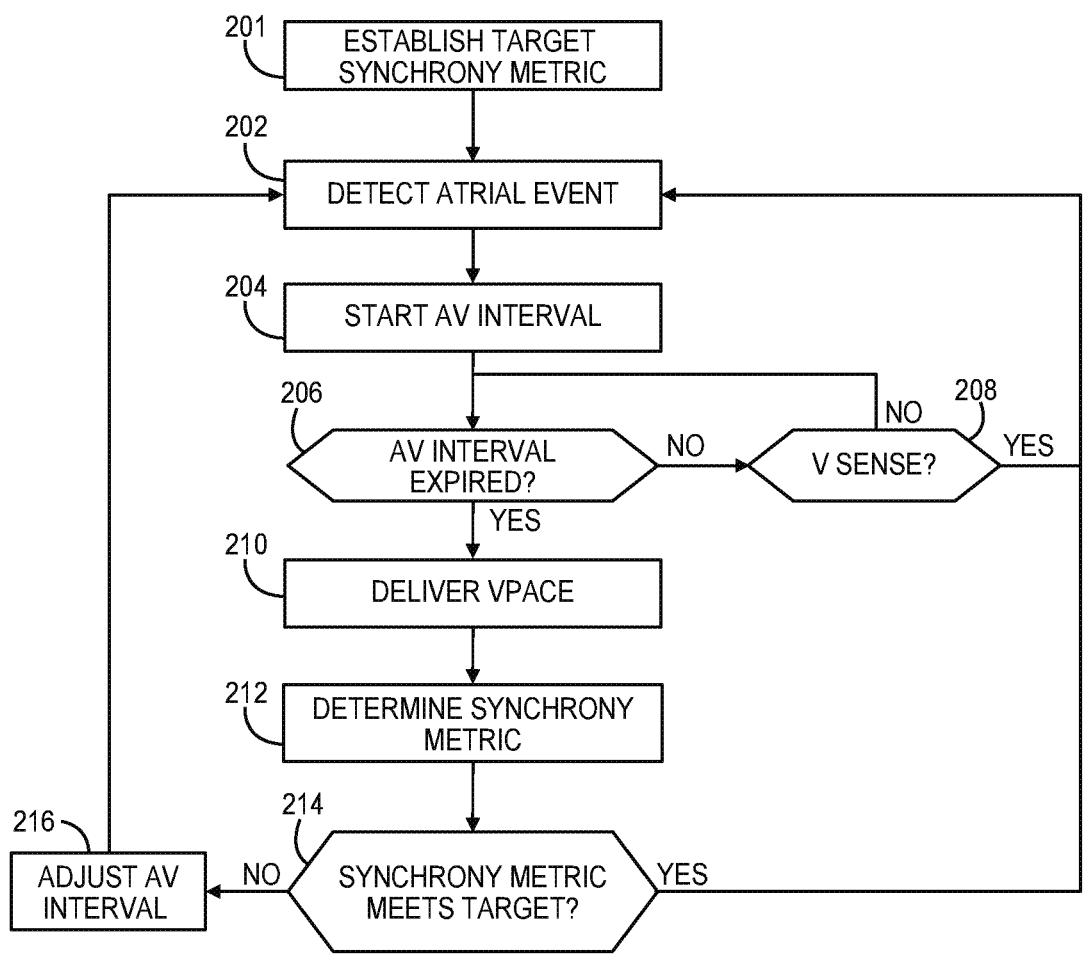
FIG. 7 is a flow chart of a method for controlling the AV interval by an intracardiac pacemaker during atrial synchronized ventricular pacing according to one example.

FIG. 7 is a flow chart 200 of a method performed by pacemaker 10 for controlling the AV interval during atrial synchronized ventricular pacing according to one example. At block 201, a target value of one or more synchrony metrics is established. As described above, the target value may be based on a value of the synchrony metric determined during intrinsic conduction to the ventricles, which may follow an atrial pacing pulse or an intrinsic sensed P-wave. For example, if the synchrony metric is the A1 signal width, the A1 signal width may be measured when ventricular pacing is not being delivered. The target value may be set to a maximum threshold value of the A1 signal width, which may be defined as a percentage of the A1 signal width or a predetermined interval greater than the A1 signal width. In this example, it is assumed that an increase in A1 signal width above the target value indicates a trend in increasing dyssynchrony of the RV and LV contractions.

In another example, if the synchrony metric is the A4-A1 interval, the A4-A1 interval may be determined during ventricular sensing (no ventricular pacing pulse delivered). A target A4-A1 interval range may be set based on the target A4-A1 interval value determined during ventricular sensing. A minimum A4-A1 interval may be defined as a first percentage of the determined A4-A1 interval during ventricular sensing and may represent a minimum time delay from the end of atrial mechanical systole until the onset of ventricular contraction. A maximum A4-A1 interval may be defined as a second percentage of the determined A4-A1 interval during ventricular sensing and may represent a maximum time delay from the end of atrial mechanical systole until the onset of ventricular contraction for promoting optimal hemodynamic function during ventricular pacing.

In other examples, the target threshold or range of one or more synchrony metrics may be programmed into memory 82 by a user at block 201, e.g., using an external programmer. The target synchrony metric value may be determined during ventricular pacing when the AV interval is determined to be optimized based on another clinical measurement or assessment, such as during an echocardiography study. The target value of the synchrony metric may be determined during ventricular pacing at the optimized AV interval and a target threshold or range based on the determined synchrony metric target value may be programmed into memory 82.

At block 202, control circuit 80 detects an atrial event. In some examples, the atrial event is an electrical event. The atrial electrical event may be an intrinsic P-wave sensed by sensing circuit 86 or an atrial pacing pulse delivered by therapy delivery circuit 84. In some examples, however, the atrial event detected at block 202 could be the A4 signal sensed from the motion signal received from motion sensor 90. Control circuit 80 starts an AV interval at block 204 in response to detecting the atrial event. The AV interval started at block 204 may be a sense AV (SAV) interval following a sensed P-wave or a paced AV (PAV) interval following a delivered atrial pacing pulse or an A4-V interval following the sensed A4 signal. The SAV interval, the PAV interval, and the A4-V pacing interval may each be different intervals to account for differences in the relative timing of the atrial and ventricular electrical events and atrial and ventricular mechanical events. Furthermore, an SAV interval may be set differently when the sensed P-wave is a sinus P-wave arising from the sinoatrial node than the SAV interval set when the sensed P-wave is an ectopic beat or premature atrial contraction (PAC). For instance, a PAC may be sensed when a P-wave is sensed consecutively following a preceding sensed P-wave or atrial pacing pulse without an intervening ventricular event. If the PAC is sensed early, e.g., during an atrial refractory period, the PAC may be ignored. However if the PAC is sensed after the atrial refractory period has expired, control circuit 80 may start an AV interval at block 204 in response to sensing the PAC at block 202. The SAV interval started in response to the PAC may be set to a different time interval than the SAV interval started in response to a sinus P-wave.

If an R-wave is sensed at block 208, e.g., a ventricular sensed event signal is received from sensing circuit 86, before the AV interval expires ("no" branch of block 206), control circuit 80 cancels the scheduled ventricular pacing pulse and returns to block 202 to wait for the next atrial event to start the next AV interval. In some examples, when an intrinsic R-wave is sensed and the target synchrony metric threshold or range is based on a synchrony metric target value determined during ventricular sensing, control circuit 80 may return to block 201 from block 208. Control circuit 80 may determine the synchrony metric value following the ventricular sensed event and update the target synchrony metric threshold or range at block 201 based on the determined value. For example, multiple synchrony metric values determined during intrinsic, sensed ventricular cycles may be stored and averaged in a first-in-first-out basis (with outliers being neglected) or a weighted combination of the most recently stored synchrony metric target value (which may be an average of multiple values) and the currently measured synchrony metric value may be determined as an updated synchrony metric target value. The target value may be used to set a target threshold or range of the synchrony metric used in controlling AV interval adjustments.

When the AV interval expires at block 206 without sensing an R-wave, a ventricular pacing pulse is delivered at block 210 by therapy delivery circuit 84. Control circuit 212 determines the synchrony metric at block 212 following the ventricular pacing pulse. In some examples, the synchrony metric may be determined beat by beat following each ventricular pacing pulse to allow AV interval adjustments as frequent as each ventricular pacing pulse delivery. In other examples, the synchrony metric is determined at block 212 when the ventricular pacing pulse that is delivered at block 210 is the nth ventricular pacing pulse, where n is a predetermined number of ventricular pacing pulses. For example, the synchrony metric may be determined every $8^{th}$ pacing pulse, every $12^{th}$ pacing pulse, every $20^{th}$ pacing pulse or other selected number of pacing pulses. In still other examples, the synchrony metric may be determined at block 212 according to a predetermined schedule, for example once per day, once per hour, once per minute or other frequency. Furthermore, it is recognized that determining the synchrony metric at block 212 may include determining the synchrony metric for multiple paced ventricular cycles and combining determined values by averaging or other statistical methods for determining a representative synchrony metric for the currently applied AV interval, which may be an SAV interval, PAV interval, PAC-AV interval or A4-V interval.

At block 214, the synchrony metric is compared to the target synchrony metric threshold or range by control circuit 80. If the synchrony metric determined at block 212 meets the target synchrony metric threshold or range established at block 201, control circuit 80 returns to block 202 to wait for the next atrial event without adjusting the AV interval. The synchrony metric determined at block 212 may not meet the target threshold or range when the synchrony metric is less than a minimum threshold established at block 201 or greater than a maximum threshold established at block 201. In response to the synchrony metric determined at block 212 not meeting the target synchrony metric requirements at block 214, control circuit 80 adjusts the AV pacing interval at block 216.

The adjustment of the AV interval may be an increase or decrease by a step interval, e.g., 10 ms, 15 ms, 20 ms, 25 ms, 30 ms, 50 ms or other selected interval. Depending on the synchrony metric value determined at block 212 and the corresponding target threshold or range, the AV interval adjustment may be an increase, e.g., when the A4-A1 interval is too short, or a decrease, e.g., when the A4-A1 interval is too long. The AV interval may be increased or decreased in one step based on the difference between the target value and the synchrony metric value determined at block 212 in some examples. In this way, the AV interval may be corrected in a single adjustment to bring the synchrony metric within a target requirement.

In some cases, it may not be obvious whether the AV interval needs to be increased or decreased or by how much. As such, the adjustment at block 216 may be a step increment or decrement and the process of blocks 202 through 216 may be repeated until the synchrony metric determined at block 212 meets the synchrony metric requirements at block 214, which may include multiple increasing and/or decreasing adjustments of the AV interval.

Figure 8:
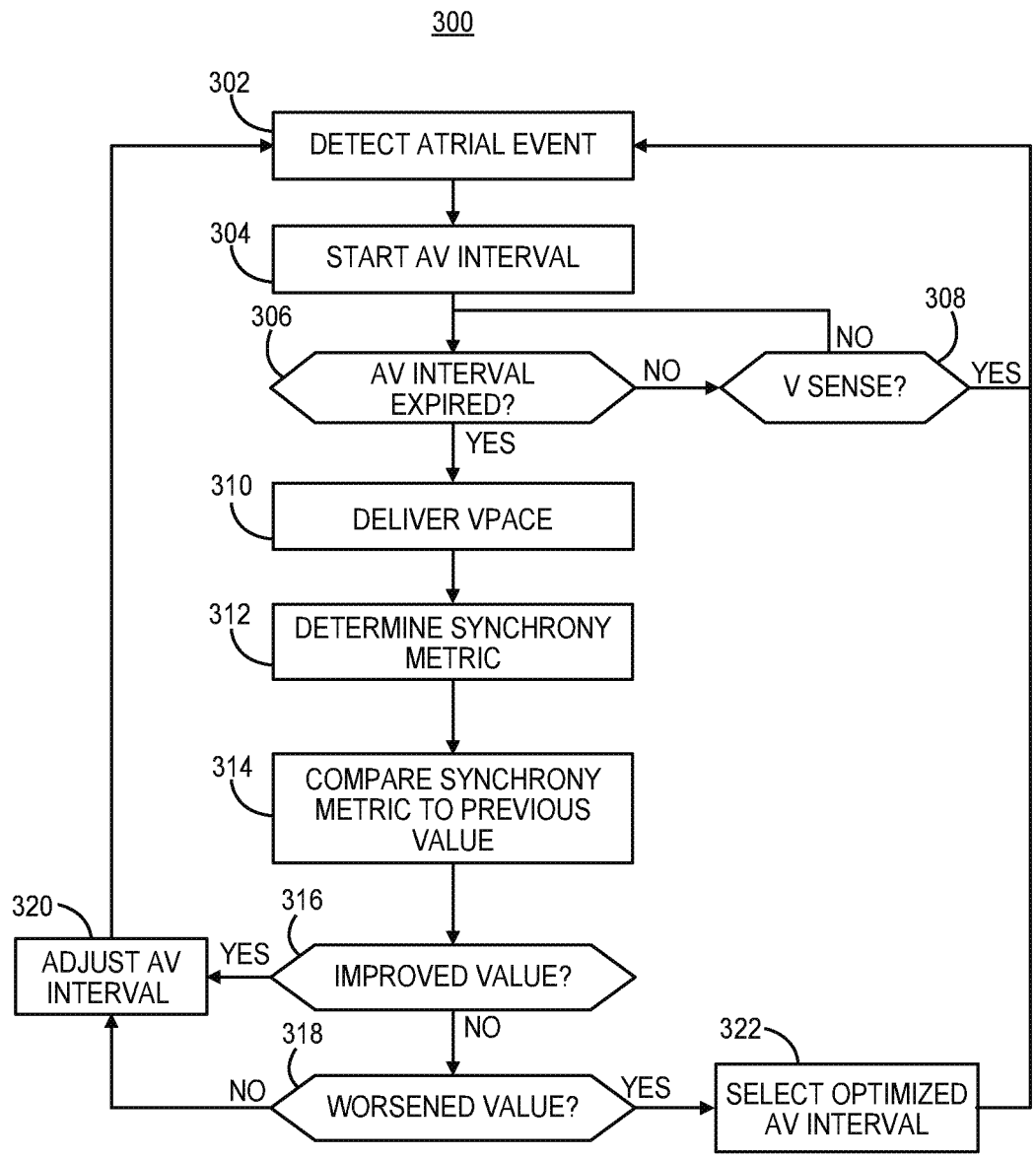
FIG. 8 is a flow chart of a method for controlling the AV interval according to another example.

FIG. 8 is a flow chart 300 of a method for controlling the AV interval by pacemaker 10 according to another example. Pacemaker 10 may be configured to learn an optimized synchrony metric value by adjusting the AV interval until a change in the synchrony metric correlated to improved heart chamber synchrony is reached, without further improvement being gained with further AV interval adjustments. Rather than establishing a target synchrony metric threshold or range based on a target value as described in conjunction with FIG. 7, control circuit 80 may determine one or more synchrony metric(s) during ventricular pacing at multiple AV interval settings and select the AV interval setting that results in a synchrony metric value considered to be the greatest improvement or more optimized than other synchrony metric values determined at other AV interval settings.

At block 302, an atrial event is detected by control circuit 80, e.g., an atrial pacing pulse, a sensed P-wave or a sensed A4 signal. The AV interval is started at block 304 by control circuit 80 in response to detecting the atrial event. If an R-wave is sensed (block 308) by the sensing circuit before the AV interval expires (block 306), e.g., when a R-wave sensed event signal is received from sensing circuit 86 during the AV interval, control circuit 80 waits for the next atrial event. The scheduled ventricular pacing pulse is withheld.

When the AV interval expires at block 306, without sensing an R-wave, the scheduled ventricular pacing pulse is delivered by therapy delivery circuit 84 at block 310. At block 312, a synchrony metric is determined by control circuit 80 from the motion signal. The synchrony metric may be any of the examples given above in conjunction with FIGS. 5 and 6, and, in some examples, more than one synchrony metric may be determined. In one example, the A4-A1 interval is determined in addition to at least one other metric of a ventricular mechanical event, such as the A1 amplitude, A1 width, A1-A2 time interval or other metric indicative of RV and LV synchrony. At block 314, each synchrony metric determined at block 312 may be compared to a previously determined synchrony metric. The comparison may be made by control circuit 80 by determining a trend or difference between the currently determined and a previously determined value of the synchrony metric.

If the currently determined value represents an improvement in heart chamber synchronization, as determined at block 316, the AV interval may be adjusted by control circuit 80 to another test interval at block 320. The AV interval may continue to be adjusted until no further improvement is achieved based on the determination at block 316. Control circuit 80 may determine that the synchrony metric is improved if the value of the metric increases or decreases compared to a previous value, depending on what the metric is. For example, an increase in A1 peak amplitude may indicate an improvement in ventricular synchrony while an increase in A1 width or area may indicate a worsened value. A ventricular mechanical event time interval, such as the Vpace-A1, Vpace-A2, or A1-A2 time interval that increases may indicate a worsened value associated with increased ventricular dyssynchrony, while a decreased ventricular time interval value may indicate an improved value associated with improved ventricular synchrony.

When the currently determined synchrony metric value is not determined by control circuit 80 to be an improved value at block 316, and is not determined to be a worsened value than the previous value (e.g., stays the same), the AV interval may be adjusted by control circuit 80 to another test setting at block 320 in the search for an AV interval that results in an improved synchrony metric. When the synchrony metric value is determined to be a worsened value than the preceding value, however, the AV interval may be adjusted back to a previous AV interval setting at block 322. The previous AV interval setting is the setting that corresponds to the most improved synchrony metric determined (so far) relative to other synchrony metric values determined for all AV intervals tested.

It is recognized that when two or more synchrony metrics are being monitored during AV interval adjustments, one synchrony metric may act as a constraint over the possible AV interval settings and maximum possible change that may be achieved in another synchrony metric. For example, the A4-A1 interval may be restricted by a minimum bound such that the AV interval cannot be decreased further in order to improve an A1 amplitude or A1 width, for instance, when the A4-A1 interval is at the minimum bound. Another synchrony metric indicative of ventricular synchrony may be optimized, e.g., minimized or maximized, within the AV interval bound defined by the minimum A4-A1 interval.

The process of FIG. 8 may be performed by pacemaker 10 on a beat by beat basis such that the AV interval may be adjusted as needed by control circuit 80 to maintain an improvement in the synchrony metric(s) being monitored. In other examples, the process of flow chart 300 may be performed on a scheduled, periodic basis so that once an optimal AV interval is found based on achieving an improved synchrony metric, the optimal AV interval may be used until the process of flow chart 300 is scheduled to be performed again. In still other examples, the process of determining a synchrony metric during ventricular pacing and adjusting an AV interval to reach an improved or target threshold or range of the synchrony metric may be performed on a triggered basis.

Figure 9:
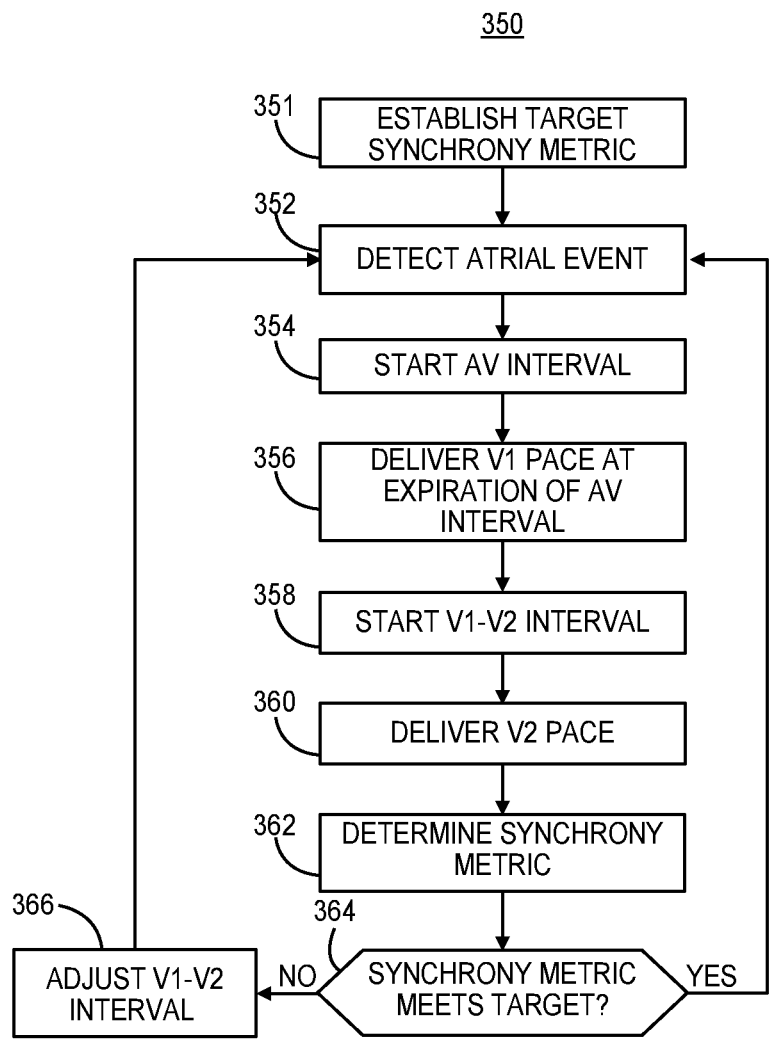
FIG. 9 is a flow chart of a method for controlling an inter-ventricular pacing interval during bi-ventricular pacing according to one example.

FIG. 9 is a flow chart 350 of a method for controlling an inter-ventricular pacing interval according to one example. Pacemaker 10 may be positioned in the right ventricle as shown in FIG. 3 to provide LV pacing using distal ventricular electrode 42. LV pacing pulses may be delivered at an AV pacing interval following a sensed A4 signal from the motion signal or following an interventricular pacing interval between the RV and the LV to provide cardiac resynchronization therapy. The interventricular pacing interval may be started in response to sensing an R-wave in the RV or in response to delivering an RV pacing pulse using the distal housing based electrode 22 and proximal housing based electrode 24. In some examples, atrial synchronized biventricular pacing is delivered by starting an AV interval in response to sensing the A4 signal from the motion signal for delivering a ventricular pacing pulse to a first ventricular chamber, the RV or the LV, then an interventricular pacing interval is started in response to the first ventricular pacing pulse for timing the delivery of a second ventricular pacing pulse to the second ventricular chamber, the other one of the LV or RV.

At block 351, a target synchrony metric value is established by control circuit 80, using any of the example techniques as described above. The target synchrony metric value is an indication of ventricular synchrony. An atrial event is detected at block 352. The atrial event may be the A4 signal corresponding to the mechanical atrial systolic event. The atrial event may be detected during the early portion of the A4 signal, e.g., prior to the A4 signal peak based on an A4 sensing threshold crossing of the motion signal, to start the AV pacing interval. The AV pacing interval may be adjusted based on a synchrony metric as described above, e.g., based on an A4-A1 time interval. The A4-A1 time interval may be a time interval from an ending time of the A4 signal to the onset of the A1 signal in order to avoid the onset of ventricular contraction before the end of the A4 signal. The ending time of the A4 signal (e.g., as shown in FIG. 5 as ending time 115) may be detected upon a return to a baseline amplitude, a negative-going crossing of a predetermined ending time threshold amplitude, or a predetermined number of sample points below a predetermined ending time threshold amplitude, as examples.

Upon expiration of the AV interval, a V1 pacing pulse is delivered by therapy delivery circuit 84 at block 356 to a first ventricular chamber (right or left). Control circuit 80 starts the inter-ventricular pacing interval (V1-V2 pacing interval) at block 358 in response to the delivery of the first V1 pacing pulse. At block 360, the second V2 pacing pulse is delivered by therapy delivery circuit 84 to the other, opposite ventricular chamber (left or right) upon the expiration of the V1-V2 pacing interval. After delivery of the biventricular pacing pulses, the synchrony metric is determined at block 362 from the motion signal. The synchrony metric may be any of the examples described above determined from the A1 and/or A2 signals as an indicator of ventricular synchrony. The synchrony metric is compared to the target value (or threshold or range based on the target value determined at block 351) by control circuit 80. If the synchrony metric does not meet the synchrony requirement, the V1-V2 pacing interval may be adjusted by control circuit 80 at block 366. If the synchrony requirement applied at block 364 is met, control circuit 80 waits to detect the next atrial event at block 352 without adjusting the V1-V2 pacing interval. The process of FIG. 9 may be repeated on a beat-by-beat basis or less frequently, e.g., every nth cardiac cycle, once per minute, once per hour, once per day, or other scheduled interval. It is recognized that the process of FIG. 7 or FIG. 8 may be combined with the process of FIG. 9 for adjusting both the AV pacing interval and the V1-V2 pacing interval in some examples.

Figure 10:
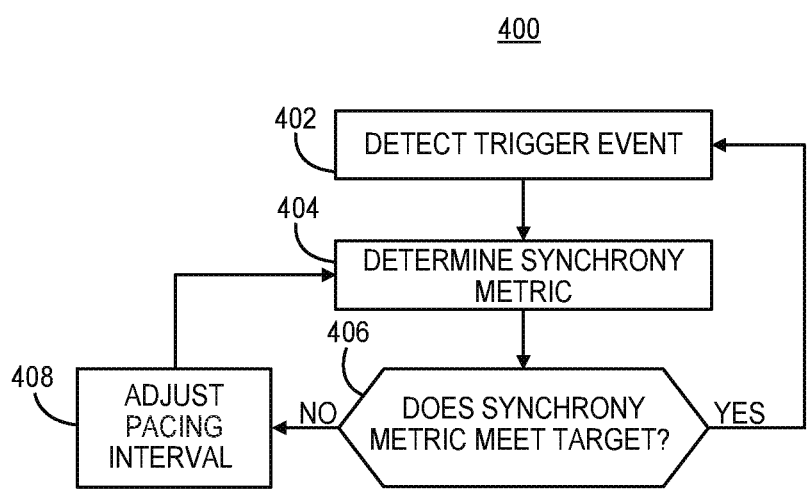
FIG. 10 is a flow chart of a method for performing pacing interval optimization on a triggered basis according to some examples.

FIG. 10 is a flow chart 400 of a method for performing pacing interval optimization by pacemaker 10 on a triggered basis. At block 402, control circuit 80 detects a trigger event for optimizing the pacing interval based on at least one synchrony metric. The pacing interval being optimized may be the AV pacing interval and/or the inter-ventricular pacing interval. The trigger event may be a change in the cardiac electrical signal or a change in the cardiac motion signal. In one example, control circuit 80 is configured to monitor the R-wave slew rate from the EGM signal received from sensing circuit 86. A change in the slew rate of the R-wave may indicate a change in ventricular synchrony. For example, a decrease in slew rate may indicate increased ventricular dyssynchrony. Other changes in the R-wave that may be detected by control circuit 80 as a triggering event may include a change in the R-wave peak amplitude and/or a change in the R-wave width. In another example, control circuit 80 may monitor the A1 signal for a change in slope or peak amplitude. Control circuit 80 may detect a trigger event at block 402 by detecting a change in the R-wave slew rate, e.g., a decrease compared to a previously determined slew rate or average slew rate. Additionally or alternatively, control circuit 80 may detect a trigger event at block 402 by detecting a change in the A1 signal slope or peak amplitude or other feature of the A1 signal compared to a previously determined feature value or average value.

When a trigger event is detected at block 402, control circuit 80 determines the synchrony metric(s) at block 404 following ventricular pacing delivered at the currently set AV pacing interval and/or V1-V2 pacing interval. The synchrony metric(s) may be determined according to any of the examples given above. Control circuit 80 compares the synchrony metric(s) to a respective target threshold or range at block 406. If the determined synchrony metric satisfies a target range or threshold, control circuit 80 returns to block 402 to wait for the next trigger event. If the synchrony metric does not satisfy a synchrony metric target range or threshold, control circuit 80 adjusts the pacing interval at block 408, then re-determines the synchrony metric at block 404 following subsequent ventricular pacing pulse(s) at the adjusted pacing interval(s). This process may continue with multiple pacing interval adjustments as needed, to one or both of the AV and inter-ventricular pacing intervals, until the synchrony metric target range(s) or threshold(s) are met at block 406 for one or more synchrony metrics.

In other examples, the process of FIG. 10 may be initiated in response to detecting a trigger event and instead of adjusting the pacing interval until a previously-established synchrony metric target threshold or range is met, control circuit 80 may adjust the pacing interval(s) to multiple settings (or combinations of AV and V1-V2 interval settings) until an improvement in the synchrony metric is detected, which may be a maximum improvement within any predefined bounds of the AV interval settings and/or the A4-A1 interval and/or upper and lower bounds of the inter-ventricular pacing interval. Depending on the synchrony metric, the synchrony metric may be minimized or maximized, within any predefined bounds of the AV interval, V1-V2 interval, and/or another synchrony metric.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units, circuits or processors associated with, for example, a medical device.

In one or more examples, the functions described may be implemented in hardware, software, firmware, or any combination thereof. If implemented in software or firmware, the functions may be stored as one or more instructions or code on a computer-readable medium and executed by a hardware-based processing unit. Computer-readable media may include non-transitory computer-readable storage media, which corresponds to a tangible medium such as data storage media (e.g., RAM, ROM, EEPROM, flash memory, or any other non-transitory medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
    a motion sensor configured to produce a motion signal comprising an atrial systolic event signal, a first ventricular systolic event signal corresponding to an onset of ventricular contraction, and a second ventricular systolic event signal corresponding to an ending of ventricular contraction;
    a therapy delivery circuit configured to generate ventricular pacing pulses, each ventricular pacing pulse being generated upon expiration of a pacing interval; and
    a control circuit configured to:
        determine a synchrony metric from the motion signal based on at least one of the first ventricular systolic event signal and the second ventricular systolic event signal following at least one ventricular pacing pulse generated by the therapy delivery circuit; and
        adjust the pacing interval based on the synchrony metric.

2. The medical device of claim 1, wherein the control circuit is configured to:
    determine the synchrony metric as a time interval from the atrial systolic event signal to the first ventricular systolic event signal;
    determine that the time interval is less than a time interval threshold; and
    increase the pacing interval in response to the time interval being less than the time interval threshold.

3. The medical device of claim 1, wherein the control circuit is configured to:

determine the synchrony metric as a time interval ending at one of the first ventricular systolic event and the second ventricular systolic event;
determine that the time interval is greater than a threshold time interval; and
adjust the pacing interval in response to the time interval being greater than the threshold time interval to decrease the synchrony metric.

4. The medical device of claim 1, wherein the control circuit is configured to:
determine the synchrony metric by determining a time interval from a first peak of the first ventricular systolic event signal to a second peak of the first ventricular systolic event signal; and
adjust the pacing interval to decrease the time interval from the first peak to the second peak.

5. The medical device of claim 1, further comprising:
a cardiac electrical signal sensing circuit configured to sense an intrinsic R-wave attendant to intrinsic depolarization of ventricular myocardium,
wherein the control circuit is further configured to:
determine a target value of the synchrony metric from the motion signal following the sensed intrinsic R-wave,
set a threshold of the synchrony metric based on the target value;
determine that the synchrony metric does not meet the threshold; and
adjust the pacing interval in response to the synchrony metric not meeting the threshold.

6. The medical device of claim 1, further comprising:
a cardiac electrical signal sensing circuit configured to sense an R-wave attendant to a depolarization of ventricular myocardium;
wherein the control circuit is further configured to:
detect a change in the R-wave sensed by the cardiac electrical signal sensing circuit; and
determine the synchrony metric from the motion signal in response to detecting the change in the R-wave.

7. The medical device of claim 6, wherein the control circuit is configured to detect the change in the R-wave by detecting a change in a slew rate of the R-wave.

8. The medical device of claim 1, further comprising:
a housing configured for implantation within an atrial chamber; and
a ventricular electrode coupled to the housing and configured to advance into ventricular tissue when the housing is implanted in the atrial chamber;
wherein the motion sensor is configured to produce an intra-atrial motion signal comprising the atrial systolic event signal, the first ventricular systolic event signal, and the second ventricular systolic event signal.

9. The pacemaker of claim 1, wherein the control circuit is configured to:
adjust the pacing interval to a plurality of settings;
determine the synchrony metric for each one of the plurality of settings of the pacing interval by determining the synchrony metric following a ventricular pacing pulse delivered at each one of the plurality of settings;
compare the synchrony metrics determined for the plurality of settings of the pacing interval;
based on the comparison of the synchrony metrics, identify one of the synchrony metrics corresponding to a greatest improvement in synchrony metric;
identify one of the plurality of settings of the pacing interval corresponding to the greatest improvement in the synchrony metric; and set the pacing interval to the identified one of the plurality of settings of the pacing interval.

10. The pacemaker of claim 1, wherein the control circuit is configured to determine the synchrony metric by:
setting a time window corresponding to at least one of the first ventricular systolic event and the second ventricular systolic event;
identifying sample points of the motion signal that are greater than a threshold amplitude during the time window; and
determining the synchrony metric based on at least a portion of the identified sample points.

11. The pacemaker of claim 1, wherein the control circuit is configured to adjust the pacing interval by adjusting at least one of an atrioventricular pacing interval and an interventricular pacing interval.

12. The pacemaker of claim 1, further comprising a cardiac electrical signal sensing circuit configured to sense an intrinsic P-wave attendant to intrinsic depolarization of atrial myocardium,
wherein:
the therapy delivery circuit is further configured to generate atrial pacing pulses;
the control circuit is further configured to:
set the pacing interval by setting an atrioventricular pacing interval;
determine a first synchrony metric from the motion signal in response to the cardiac electrical signal sensing circuit sensing an intrinsic P-wave;
adjust the pacing interval by adjusting a first atrioventricular pacing interval based on the first synchrony metric;
determine a second synchrony metric from the motion signal in response to the therapy delivery circuit generating an atrial pacing pulse; and
adjust a second atrioventricular pacing interval based on the second synchrony metric.

13. The pacemaker of claim 1, wherein:
the therapy delivery circuit is configured to:
generate a first ventricular pacing pulse delivered to a first ventricular pacing site; and
generate a second ventricular pacing pulse upon expiration of an interventricular pacing interval started upon delivery of the first ventricular pacing pulse, the second ventricular pacing pulse delivered to a second ventricular pacing site;
the control circuit is further configured to:
start the interventricular pacing interval in response to the first ventricular pacing pulse being delivered by the therapy delivery circuit;
determine the synchrony metric from the motion signal after the second ventricular pacing pulse; and
adjust the pacing interval by adjusting the interventricular pacing interval based on the synchrony metric.

14. The pacemaker of claim 1, wherein:
the therapy delivery circuit is configured to:
generate a first ventricular pacing pulse upon expiration of an atrioventricular pacing interval; and
generate a second ventricular pacing pulse upon expiration of an interventricular pacing interval started upon delivery of the first ventricular pacing pulse;
the control circuit is further configured to:
sense the atrial systolic event from the motion signal;
set the atrioventricular pacing interval in response to sensing the atrial systolic event;

set the interventricular pacing interval in response to the first ventricular pacing pulse being generated;
determine the synchrony metric from the motion signal after the second ventricular pacing pulse delivered upon expiration of the interventricular pacing interval; and
adjust the pacing interval by adjusting the interventricular pacing interval based on the synchrony metric.

15. A method, comprising:
producing a motion signal comprising an atrial systolic event signal, a first ventricular systolic event signal corresponding to an onset of ventricular contraction, and a second ventricular systolic event signal corresponding to an ending of ventricular contraction;
generating a ventricular pacing pulse upon expiration of a pacing interval;
determining a synchrony metric from the motion signal based on at least one of the first ventricular systolic event signal and the second ventricular systolic event signal following the ventricular pacing pulse; and
adjusting the pacing interval based on the synchrony metric.

16. The method of claim 15, further comprising:
determining the synchrony metric as a time interval from the atrial systolic event signal to the first ventricular systolic event signal;
determining that the time interval is less than a time interval threshold; and
increasing the pacing interval in response to the time interval being less than the time interval threshold.

17. The method of claim 15, further comprising:
determining the synchrony metric as a time interval ending at one of the first ventricular systolic event and the second ventricular systolic event;
determining that the time interval is greater than a threshold time interval; and
adjusting the pacing interval in response to the time interval being greater than the threshold time interval to decrease the synchrony metric.

18. The method of claim 15, further comprising:
determining the synchrony metric by determining a time interval from a first peak of the first ventricular systolic event signal to a second peak of the first ventricular systolic event signal; and
adjusting the pacing interval to decrease the time interval from the first peak to the second peak.

19. The method of claim 15, further comprising:
sensing an intrinsic R-wave attendant to intrinsic depolarization of ventricular myocardium;
determining a target value of the synchrony metric from the motion signal following the intrinsic R-wave;
setting a threshold of the synchrony metric based on the target value;
determining that the synchrony metric does not meet the threshold; and
adjusting the pacing interval in response to the synchrony metric not meeting the threshold.

20. The method of claim 15, further comprising:
sensing an R-wave attendant to a depolarization of ventricular myocardium;
detecting a change in the R-wave; and
determining the synchrony metric from the motion signal in response to detecting the change in the R-wave.

21. The method of claim 20, further comprising detecting the change in the R-wave by detecting a change in a slew rate of the R-wave.

22. The method of claim 15, wherein:
producing the motion signal comprises producing an intra-atrial motion signal comprising the atrial systolic event signal, the first ventricular systolic event signal, and the second ventricular systolic event signal; and
delivering the generated ventricular pacing pulses via a plurality of housing-based electrodes when the housing is implanted in an atrial chamber.

23. The method of claim 15, further comprising:
adjusting the pacing interval to a plurality of settings;
determining the synchrony metric for each one of the plurality of settings of the pacing interval by determining the synchrony metric following a ventricular pacing pulse delivered at each one of the plurality of settings;
comparing the synchrony metrics determined for the plurality of settings of the pacing interval,
based on the comparing, identifying one of the synchrony metrics corresponding to a greatest improvement in the synchrony metric;
identifying one of the plurality of settings of the pacing interval corresponding to the greatest improvement in the synchrony metric; and
setting the pacing interval to the identified one of the plurality of settings of the pacing interval.

24. The method of claim 15, wherein determining the synchrony metric comprises:
setting a time window corresponding to at least one of the first ventricular systolic event and the second ventricular systolic event;
identifying sample points of the motion signal that are greater than a threshold amplitude during the time window; and
determining the synchrony metric from at least a portion of the identified sample points.

25. The method of claim 15, wherein adjusting the pacing interval comprises adjusting at least one of an atrioventricular pacing interval and an interventricular pacing interval.

26. The method of claim 15, further comprising:
sensing an intrinsic P-wave attendant to intrinsic depolarization of atrial myocardium,
setting the pacing interval by setting an atrioventricular pacing interval;
determining a first synchrony metric from the motion signal in response to sensing the intrinsic P-wave;
adjusting the pacing interval by adjusting a first atrioventricular pacing interval based on the first synchrony metric;
generating an atrial pacing pulse;
determining a second synchrony metric from the motion signal in response to the generated atrial pacing pulse; and
adjusting a second atrioventricular pacing interval based on the second synchrony metric.

27. The method of claim 15, further comprising:
generate a first ventricular pacing pulse delivered to a first ventricular pacing site;
starting an interventricular pacing interval in response to the first ventricular pacing pulse being generated;
generating a second ventricular pacing pulse upon expiration of the interventricular pacing interval, the second ventricular pacing pulse delivered to a second ventricular pacing site;
determining the synchrony metric from the motion signal after generating the second ventricular pacing pulse; and
adjusting the pacing interval by adjusting the interventricular pacing interval based on the synchrony metric.

28. The method of claim 15, further comprising:
sensing the atrial systolic event from the motion signal;
setting an atrioventricular pacing interval in response to sensing the atrial systolic event;
generating a first ventricular pacing pulse upon expiration of the atrioventricular pacing interval;
setting an interventricular pacing interval in response to the first ventricular pacing pulse being generated;
generating a second ventricular pacing pulse upon expiration of the interventricular pacing interval;
determining the synchrony metric from the motion signal after the second ventricular pacing pulse; and
adjusting the pacing interval by adjusting the interventricular pacing interval based on the synchrony metric.

29. A non-transitory computer-readable storage medium storing a set of instructions, which when executed by a pacemaker, cause the pacemaker to:
produce a motion signal comprising an atrial systolic event signal, a first ventricular systolic event signal corresponding to an onset of ventricular contraction, and a second ventricular systolic event signal corresponding to an ending of ventricular contraction;
generate a ventricular pacing upon expiration of a pacing interval;
determine a synchrony metric from the motion signal based on at least one of the first ventricular systolic event signal and the second ventricular systolic event signal following the ventricular pacing pulse; and
adjust the pacing interval based on the synchrony metric.

* * * * *